US012577241B2

(12) United States Patent
Tomida et al.

(10) Patent No.: US 12,577,241 B2
(45) Date of Patent: Mar. 17, 2026

(54) POLYCYCLIC PYRIDOPYRAZINE DERIVATIVE

(71) Applicant: Shionogi & Co., Ltd., Osaka (JP)

(72) Inventors: Yutaka Tomida, Osaka (JP); Takashi Kawasuji, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 903 days.

(21) Appl. No.: 17/779,960

(22) PCT Filed: Nov. 27, 2020

(86) PCT No.: PCT/JP2020/044138

§ 371 (c)(1),
(2) Date: May 25, 2022

(87) PCT Pub. No.: WO2021/107065

PCT Pub. Date: Jun. 3, 2021

(65) Prior Publication Data

US 2023/0058677 A1 Feb. 23, 2023

(30) Foreign Application Priority Data

Nov. 28, 2019 (JP) ................................ 2019-214883

(51) Int. Cl.

| | |
|---|---|
| ***C07D 471/04*** | (2006.01) |
| ***C07D 471/08*** | (2006.01) |
| ***C07D 491/147*** | (2006.01) |
| ***C07D 491/22*** | (2006.01) |
| *A61K 31/4985* | (2006.01) |
| *A61P 31/18* | (2006.01) |
| *A61P 43/00* | (2006.01) |

(52) U.S. Cl.

CPC ......... *C07D 471/04* (2013.01); *C07D 491/22* (2013.01)

(58) Field of Classification Search

CPC .. C07D 471/04; C07D 491/22; C07D 471/08; C07D 491/147

See application file for complete search history.

(56) References Cited

U.S. PATENT DOCUMENTS

| | | | | |
|---|---|---|---|---|
| 9,522,912 | B2 * | 12/2016 | Bacon | A61P 43/00 |
| 9,951,079 | B2 * | 4/2018 | Embrey | A61K 31/5383 |
| 2009/0143356 | A1 | 6/2009 | Yoshida et al. | |
| 2013/0096109 | A1 | 4/2013 | Hattori et al. | |
| 2014/0221355 | A1 | 8/2014 | Lazerwith et al. | |
| 2016/0176870 | A1 | 6/2016 | Bacon et al. | |
| 2017/0226128 | A1 | 8/2017 | Yoshinaga et al. | |
| 2017/0305923 | A1 | 10/2017 | Embrey et al. | |
| 2018/0194774 | A1 | 7/2018 | Yu et al. | |

FOREIGN PATENT DOCUMENTS

| | | |
|---|---|---|
| EP | 1 544 199 | 6/2005 |
| EP | 1 852 434 | 11/2007 |
| EP | 1 950 212 | 7/2008 |
| EP | 2 540 720 | 1/2013 |
| EP | 2 774 928 | 9/2014 |
| EP | 2 940 019 | 11/2015 |
| EP | 3 196 201 | 7/2017 |
| EP | 3 805 220 | 4/2021 |
| EP | 3 805 221 | 4/2021 |
| EP | 4 066 839 | 10/2022 |
| JP | 2016-508134 | 3/2016 |
| JP | 2017-538713 | 12/2017 |
| JP | 2021-91670 | 6/2021 |
| JP | 2021-91671 | 6/2021 |

(Continued)

OTHER PUBLICATIONS

International Search Reported dated Jan. 19, 2021 in International (PCT) Application No. PCT/JP2020/044138.

Latest medicinal chemistry, 1998, vol. P476, pp. 494-495, with English translation.

Separation of optical isomers, 1989, pp. 16-17, with English translation.

Experimental Report Filed in Response to Opposition to European Patent No. 1950212, pp. 1-38, Experimental Report Assay Methods (May 11, 2017).

Response to Opposition Filed in European Patent No. 1950212, pp. 1-11 (May 11, 2017).

(Continued)

*Primary Examiner* — Bruck Kifle

*Assistant Examiner* — Kevin S Martin

(74) *Attorney, Agent, or Firm* — WENDEROTH, LIND & PONACK, L.L.P.

(57) ABSTRACT

The present invention provides a compound represented by the following Formula (I):

(I)

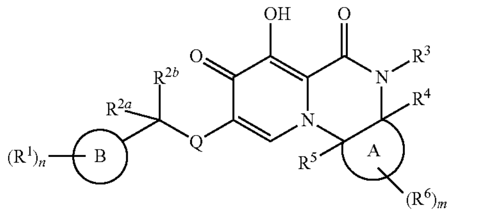

wherein ring A is a C5-C7 non-aromatic carbocycle or a 5- to 7-membered non-aromatic heterocycle; ring B is a benzene ring or the like; Q is —NHC(O)— or a 5-membered aromatic heterocycle; $R^1$ is each independently halogen or the like; $R^{2a}$ and $R^{2b}$ are each independently hydrogen, alkyl, or haloalkyl; $R^3$ is alkyl or the like; $R^4$ and $R^5$ are each independently hydrogen or the like; $R^6$ is each independently halogen, alkyl, haloalkyl, alkyloxy, haloalkyloxy, or alkyloxyalkyl; n is an integer of 1 to 3; and m is an integer of 0 to 3.

14 Claims, No Drawings

(56) References Cited

FOREIGN PATENT DOCUMENTS

| | | |
|---|---|---|
| WO | 2004/024078 | 3/2004 |
| WO | 2004/058756 | 7/2004 |
| WO | 2005/016927 | 2/2005 |
| WO | 2006/088173 | 8/2006 |
| WO | 2006/116764 | 11/2006 |
| WO | 2007/049675 | 5/2007 |
| WO | 2011/105590 | 9/2011 |
| WO | 2011/129095 | 10/2011 |
| WO | 2013/054862 | 4/2013 |
| WO | 2014/099586 | 6/2014 |
| WO | 2014/100323 | 6/2014 |
| WO | 2014/104279 | 7/2014 |
| WO | 2014/183532 | 11/2014 |
| WO | 2014/200880 | 12/2014 |
| WO | 2015/006731 | 1/2015 |
| WO | 2015/006733 | 1/2015 |
| WO | 2015/039348 | 3/2015 |
| WO | 2015/048363 | 4/2015 |
| WO | 2015/089847 | 6/2015 |
| WO | 2015/095258 | 6/2015 |
| WO | 2015/199167 | 12/2015 |
| WO | 2016/027879 | 2/2016 |
| WO | 2016/090545 | 6/2016 |
| WO | 2016/094197 | 6/2016 |
| WO | 2016/094198 | 6/2016 |
| WO | 2016/106237 | 6/2016 |
| WO | 2016/154527 | 9/2016 |
| WO | 2016/161382 | 10/2016 |
| WO | 2016/187788 | 12/2016 |
| WO | 2016/191239 | 12/2016 |
| WO | 2017/087256 | 5/2017 |
| WO | 2017/087257 | 5/2017 |
| WO | 2017/106071 | 6/2017 |
| WO | 2017/113288 | 7/2017 |
| WO | 2017/116928 | 7/2017 |
| WO | 2018/102485 | 6/2018 |
| WO | 2018/102634 | 6/2018 |
| WO | 2019/160783 | 8/2019 |
| WO | 2019/209667 | 10/2019 |
| WO | 2019/223408 | 11/2019 |
| WO | 2019/230857 | 12/2019 |
| WO | 2019/236396 | 12/2019 |
| WO | 2019230858 | 12/2019 |
| WO | 2020/197991 | 10/2020 |
| WO | 2021/173522 | 9/2021 |
| WO | 2022/072520 | 4/2022 |

OTHER PUBLICATIONS

Further Experimental Report Filed in European Patent No. 1950212, pp. 1-2 (Oct. 26, 2017).

International Preliminary Report on Patentability and Written Opinion of the International Searching Authority issued May 17, 2022 in International (PCT) Application No. PCT/JP2020/044138.

* cited by examiner

POLYCYCLIC PYRIDOPYRAZINE DERIVATIVE

TECHNICAL FIELD

The present invention relates to a novel compound having an antiviral effect. More specifically, the present invention relates to a polycyclic pyridopyrazine derivative having HIV integrase inhibitory activity and a medicament, particularly, an anti-HIV drug including thereof.

BACKGROUND ART

Among viruses, human immunodeficiency virus (hereinafter, abbreviated to HIV), one type of retrovirus, is known to cause acquired immunodeficiency syndrome (hereinafter, abbreviated to AIDS). Various guidelines currently recommend naive patients for combinations of an integrase inhibitor (dolutegravir, etc.) as a principal drug with two nucleic acid reverse transcriptase inhibitors (ABC+3TC, FTC+TAF, etc.) differing in resistance profile, as a therapeutic drug for this AIDS. Because of strong efficacy and high safety, these combinations have a high satisfaction level as compared with initial therapeutic drugs. Meanwhile, the start of treatment upon detection of HIV infection is recommended owing to the emergence of such a safe drug and good prognosis. In addition, a medication period becomes long because people infected with HIV have an average life expectancy closer to that of healthy people. If adverse reactions of the nucleic acid reverse transcriptase inhibitors occur or once a resistant virus appears due to the long-term medication, there is no further convenient treatment method. Therefore, there is a move afoot to leave the nucleic acid reverse transcriptase inhibitors unused. Hence, the establishment of two-drug treatment with two principal drugs is desired. Thus, the development of a principal drug that can be combined with the integrase inhibitor is desired. Furthermore, the development of a therapeutic drug with a longer medication interval, i.e., a long-acting injection with which treatment is completed merely by one injection at 1-month or longer intervals is desired for improving medication fatigue ascribable to the long-term medication and improving QOL (quality of life) of patients in such a way that the patients more enjoy daily life.

In order to meet such demands, an integrase inhibitor cabotegravir is under development as a long-acting injection at Ph3. Also, non-nucleic acid reverse transcriptase inhibitor rilpivirine is also under development as a long-acting injection. The establishment of a treatment method is being attempted using these two drugs. However, these drugs are injected once a month or two months and need to be injected at a total of 3 or 4 sites with pain. Hence, the development of a drug with which treatment is completed by one injection per 3 months with less pain at a lower dose is desired for further improving QOL of patients.

Raltegravir and elvitegravir as the first-generation oral agents and dolutegravir as the second-generation oral agent have already been launched as integrase inhibitors. When a naive patient uses dolutegravir, no resistant mutation appears. However, dolutegravir, when used in the treatment of a patient infected with a resistant virus to the first-generation integrase inhibitor, may be no longer effective due to the further addition of a resistant mutation. Hence, the development of an inhibitor having a higher resistance barrier than that of dolutegravir is also desired.

Bicyclic or more cyclic carbamoylpyridone derivatives are known as one of the anti-HIV drugs having an integrase inhibitory effect (Patent Documents 1 to 29). Among them, Patent Documents 9 and 20 describe fused tricyclic carbamoylpyridopyrazine derivatives. Patent Document 22 describes a fused tetracyclic carbamoylpyridopyrazine derivative.

Further, pyridone derivatives whose side chain is a heterocycle are known as one of the anti-HIV drugs having an integrase inhibitory effect (Patent Documents 5, 8, 9, 12, 13, 19, 23, 24, 27, and 30 to 33). Among them, Patent Document 9 describes a fused tricyclic pyridopyrazine derivative.

PRIOR ART REFERENCES

Patent Documents

[Patent Document 1] International Publication WO 2006/088173A

[Patent Document 2] International Publication WO 2006/116764A

[Patent Document 3] International Publication WO 2007/049675A

[Patent Document 4] International Publication WO 2011/129095A

[Patent Document 5] International Publication WO 2014/099586A

[Patent Document 6] International Publication WO 2014/100323A

[Patent Document 7] International Publication WO 2014/104279A

[Patent Document 8] International Publication WO 2014/183532A

[Patent Document 9] International Publication WO 2014/200880A

[Patent Document 10] International Publication WO 2015/039348A

[Patent Document 11] International Publication WO 2015/048363A

[Patent Document 12] International Publication WO 2015/089847A

[Patent Document 13] International Publication WO 2015/095258A

[Patent Document 14] International Publication WO 2015/006731A

[Patent Document 15] International Publication WO 2015/006733A

[Patent Document 16] International Publication WO 2015/199167A

[Patent Document 17] International Publication WO 2016/090545A

[Patent Document 18] International Publication WO 2016/094198A

[Patent Document 19] International Publication WO 2016/094197A

[Patent Document 20] International Publication WO 2016/106237A

[Patent Document 21] International Publication WO 2016/154527A

[Patent Document 22] International Publication WO 2016/161382A

[Patent Document 23] International Publication WO 2016/187788A

[Patent Document 24] International Publication WO 2016/191239A

[Patent Document 25] International Publication WO 2017/087256A

[Patent Document 26] International Publication WO 2017/087257A

[Patent Document 27] International Publication WO 2017/106071A

[Patent Document 28] International Publication WO 2017/113288A

[Patent Document 29] International Publication WO 2017/116928A

[Patent Document 30] International Publication WO 2005/016927A

[Patent Document 31] International Publication WO 2011/105590A

[Patent Document 32] International Publication WO 2013/054862A

[Patent Document 33] International Publication WO 2016/027879A

SUMMARY OF THE INVENTION

Problems to be Solved by the Invention

An object of the present invention is to provide a novel long-acting compound having integrase inhibitory activity with a high resistance barrier.

Means for Solving the Problem

The present inventors have conducted diligent studies and consequently found that a novel pyridopyrazine derivative has an integrase inhibitory effect with a high resistance barrier. The present inventors have further discovered that the compounds of the present invention and a medicament including thereof are useful as an antiviral drug (e.g., an anti-retrovirus drug, an anti-HIV drug, an anti-HTLV-1 (human T cell leukemia virus type 1) drug, an anti-FIV (feline immunodeficiency virus) drug, and an anti-SIV (simian immunodeficiency virus) drug), particularly, an anti-HIV drug, an anti-AIDS drug, or a therapeutic drug for related diseases thereof, etc., completing the present invention given below.

The present invention provides aspects given below.

[1] A compound represented by Formula (I):

[Chemical Formula 1]

(I)

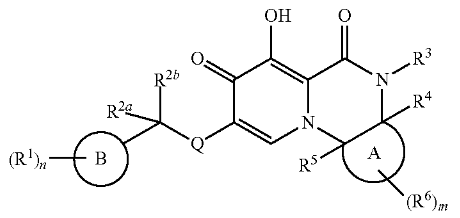

wherein ring A is a C5-C7 non-aromatic carbocycle or a 5- to 7-membered non-aromatic heterocycle, and the non-aromatic carbocycle and the non-aromatic heterocycle may be further fused with a benzene ring, a 3- to 7-membered non-aromatic carbocycle, or a 3- to 7-membered non-aromatic heterocycle and may form a spiro ring of a 3- to 7-membered non-aromatic carbocycle and a 3- to 7-membered non-aromatic heterocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^4$ and $R^5$ are each independently hydrogen or alkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge which may have an intervening heteroatom;

n is an integer of 1 to 3; and m is an integer of 0 to 3, provided that, when m is 0, a) the ring B is a pyridine ring, b) the ring A is a C5-C7 non-aromatic carbocycle, the non-aromatic carbocycle may be further fused with a benzene ring, a 3- to 7-membered non-aromatic carbocycle, or a 3- to 7-membered non-aromatic heterocycle and may form a spiro ring of a 3- to 7-membered non-aromatic carbocycle and a 3- to 7-membered non-aromatic heterocycle, and Q is a 5-membered aromatic heterocycle, c) the ring A is a C5-C7 non-aromatic carbocycle, the non-aromatic carbocycle may be further fused with a benzene ring, a 3- to 7-membered non-aromatic carbocycle, or a 3- to 7-membered non-aromatic heterocycle and may form a spiro ring of a 3- to 7-membered non-aromatic carbocycle and a 3- to 7-membered non-aromatic heterocycle, Q is —NHC(O)—, and a group represented by the following formula

[Chemical Formula 2]

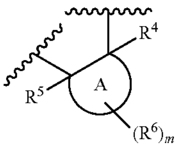

is

[Chemical Formula 3]

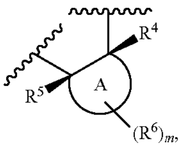

or d) the ring A is a 5- to 7-membered non-aromatic heterocycle, the non-aromatic heterocycle may be further fused with a benzene ring, a 3- to 7-membered non-aromatic carbocycle or a 3- to 7-membered non-aromatic heterocycle and may form a spiro ring of a 3- to 7-membered non-aromatic carbocycle and a 3- to 7-membered non-aromatic heterocycle, and Q is a 5-membered aromatic heterocycle, and a group represented by the following formula

[Chemical Formula 4]

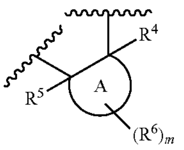

is

-continued

[Chemical Formula 5]

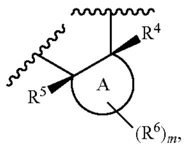

provided that the following compounds are excluded:

[Chemical Formula 6]

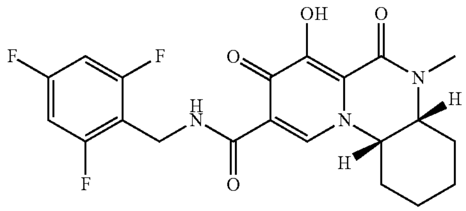

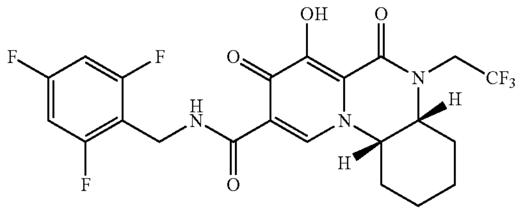

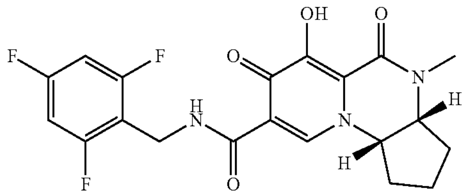

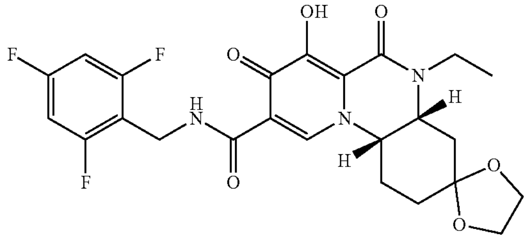

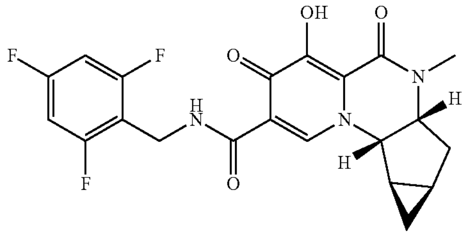

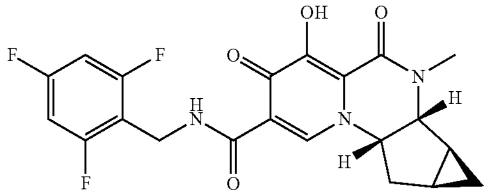

-continued

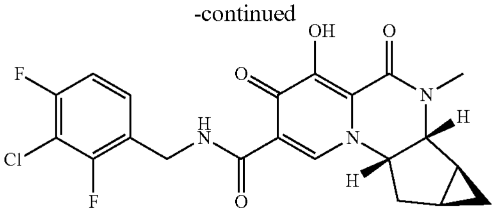

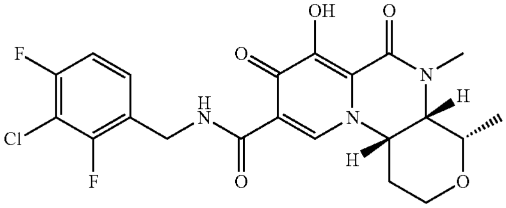

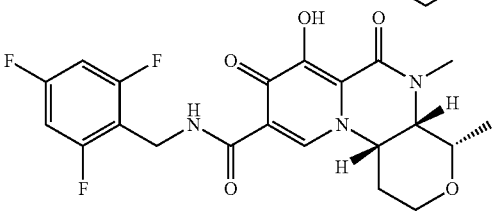

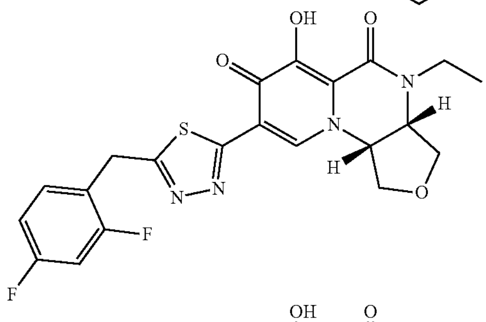

and

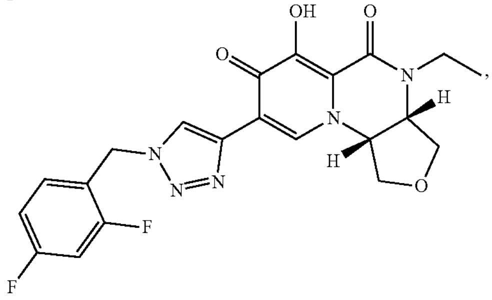

, or a pharmaceutically acceptable salt thereof.

[2] The compound according to [1], or a pharmaceutically acceptable salt thereof, wherein the ring A is a C5-C7 non-aromatic carbocycle, and $R^6$ is each independently halogen, alkyl, haloalkyl, alkyloxy, haloalkyloxy, or alkyloxyalkyl, or two $R^6$s bonded to a non-adjacent atom are taken together with each other to form a C1-C3 bridge.

[3] The compound according to [1] or [2], or a pharmaceutically acceptable salt thereof, wherein $R^4$ and $R^5$ are each hydrogen.

[4] The compound according to any one of [1] to [3], or a pharmaceutically acceptable salt thereof, wherein $R^3$ is alkyl.

[5] The compound according to any one of [1] to [4], or a pharmaceutically acceptable salt thereof, wherein $R^1$ is each independently halogen.

[6] The compound according to any one of [1] to [5], or a pharmaceutically acceptable salt thereof, wherein $R^{2a}$ is hydrogen and $R^{2b}$ is hydrogen or alkyl.

[7] The compound according to any one of [1] to [6], or a pharmaceutically acceptable salt thereof, wherein Q is —NHC(O)—.

[8] The compound according to any one of [1] to [6], or a pharmaceutically acceptable salt thereof, wherein Q is the following rings (the left bond binds to $CR^{2a}R^{2b}$):

[Chemical Formula 7]

(1)

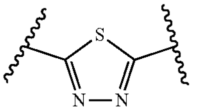

(2)

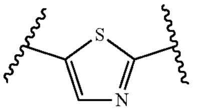

(20)

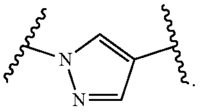

[9] The compound according to any one of [1] to [8], or a pharmaceutically acceptable salt thereof, wherein a stereochemistry of the carbon atom adjacent to $R^4$ and $R^5$ is as follows:

[Chemical Formula 8]

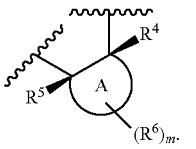

[10] A compound represented by Formula (IA):

[Chemical Formula 9]

(IA)

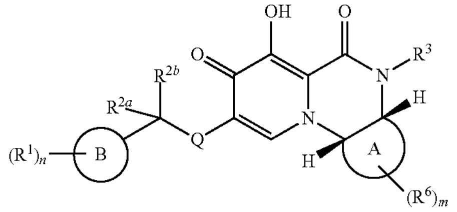

wherein ring A is a C5-C6 non-aromatic carbocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^6$ is each independently halogen, alkyl, haloalkyl, alkyloxy, haloalkyloxy, or alkyloxyalkyl; or p two $R^6$s bonded to a non-adjacent atom may be taken together with each other to form a C1-C3 bridge;

n is an integer of 1 to 3; and m is an integer of 0 to 2, provided that the following compounds are excluded:

[Chemical Formula 10]

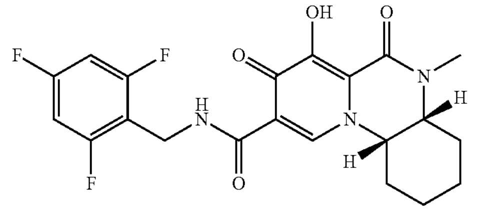

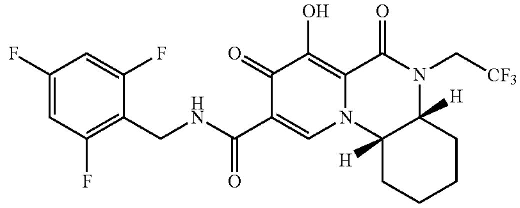

and

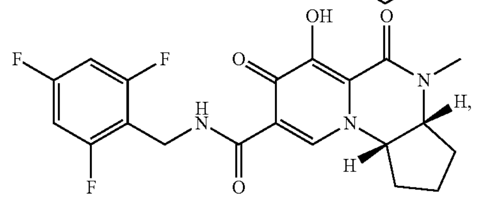

or a pharmaceutically acceptable salt thereof.

[11] The compound according to [10], or a pharmaceutically acceptable salt thereof, wherein $R^3$ is alkyl.

[12] The compound according to [10] or [11], or a pharmaceutically acceptable salt thereof, wherein $R^1$ is each independently halogen.

[13] The compound according to any one of [10] to [12], or a pharmaceutically acceptable salt thereof, wherein $R^{2a}$ is hydrogen and $R^{2b}$ is hydrogen or alkyl.

[14] The compound according to any one of [10] to [13], or a pharmaceutically acceptable salt thereof, wherein Q is —NHC(O)—.

[15] The compound according to any one of [10] to [13], or a pharmaceutically acceptable salt thereof, wherein Q is the following rings (the left bond binds to $CR^{2a}R^{2b}$):

[Chemical Formula 11]

(1)

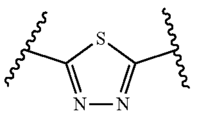

(2)

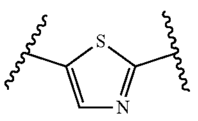

(20)

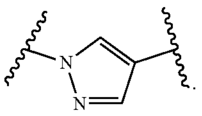

[16] The compound according to any one of [1] to [15], or a pharmaceutically acceptable salt thereof, wherein the ring B is a benzene ring.

[17] A pharmaceutical composition comprising the compound according to any one of [1] to [16] or a pharmaceutically acceptable salt thereof.

[18] The pharmaceutical composition according to [17], wherein the pharmaceutical composition is an anti-HIV agent.

[19] The pharmaceutical composition according to [17], wherein the pharmaceutical composition is an HIV integrase inhibitor.

[20] An HIV integrase inhibitor comprising the compound according to any one of [1] to [16] or a pharmaceutically acceptable salt thereof.

[21] A method for treating and/or preventing HIV infection, comprising administering the compound according to any one of [1] to [16], or a pharmaceutically acceptable salt thereof.

[22] The compound according to any one of [1] to [16], or a pharmaceutically acceptable salt thereof, for use in treating and/or preventing HIV infection.

The present invention further provides a method for preventing or treating HIV infection, comprising administering an effective amount of the compound to a human.

The present invention further provides the compound for use as an anti-HIV drug.

Effect of the Invention

The compound of the present invention has integrase inhibitory activity and/or cell proliferation inhibitory activity against viruses, in particular, HIV and drug-resistant strains thereof. Thus, the compound of the present invention is useful in preventing or treating various diseases, viral infections (e.g., AIDS), and the like with which integrase is associated. More preferably, the compound of the present invention is useful as a long-acting integrase inhibitor. Furthermore, the compound of the present invention is also excellent in resistance profile that the compound cannot easily cause a new HIV-resistant virus, and the like. Further preferably, the compound of the present invention has a preventive or therapeutic effect on HIV drug-resistant virus. Still further preferably, the compound of the present invention has small clearance, a long in vivo half-life, and excellent solubility, or metabolic stability, etc. and is also useful as a medicament with less concerns about cytotoxicity or a side effect (e.g., CYP inhibition, mutagenicity, the QT interval prolongation of the electrocardiogram, and arrhythmia).

MODE FOR CARRYING OUT THE INVENTION

The meaning of each term used in the present description is explained below. Unless particularly stated otherwise, each term is used in the same sense, either alone or in combination with other terms.

The term "consisting of" means having only the constituent elements.

The term "comprising" means not restricting with components and not excluding undescribed factors.

The term "halogen" includes a fluorine atom, a chlorine atom, a bromine atom, and an iodine atom. In particular, a fluorine atom and a chlorine atom are preferable.

"Alkyl" includes a linear or branched hydrocarbon group having 1 to 15 carbon atoms, preferably 1 to 10 carbon atoms, more preferably 1 to 6 carbon atoms, and further preferably 1 to 4 carbon atoms. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

The term "non-aromatic carbocycle" means a cyclic saturated hydrocarbon ring which is monocyclic.

Examples include cyclopentane, cyclohexane, and cycloheptane.

The term "5-membered aromatic heterocycle" means a 5-membered aromatic heterocycle containing one or more, same or different heteroatom(s) selected independently from O, S and N.

Examples of the 5-membered aromatic heterocycle include pyrrole, imidazole, pyrazole, triazole, tetrazole, furan, thiophen, isoxazole, oxazole, oxadiazole, isothiazole, thiazole, and thiadiazole.

The term "non-aromatic heterocycle" means a non-aromatic ring, which is monocyclic, containing one or more, same or different heteroatom(s) selected independently from O, S and N.

Examples of the 5-membered non-aromatic heterocycle include oxathiolane, thiazolidine, pyrrolidine, pyrroline, imidazolidine, imidazoline, pyrazolidine, pyrazoline, THF, dihydrothiazol, tetrahydrothiazol, tetrahydroisothiazole, dioxolane, dioxole, and thiolane. Examples of the 6-membered non-aromatic heterocycle include dioxane, thiane, piperidine, piperazine, morpholine, thiomorpholine, dihydropyridine, tetrahydropyridine, tetrahydropyran, tetrahydrooxazine, tetrahydropyridazine, hexahydropyrimidine, dioxazine, thiin, and thiazine. Examples of the 7-membered non-aromatic heterocycle include hexahydroazepine, hexahydrodiazepine, and oxepane.

The term "C1-C3 bridge which may have an intervening heteroatom" means C1-C3 alkylene containing one or more, same or different heteroatom(s) selected independently from O, S and N.

A preferred embodiment of each symbol in the compound represented by Formula (I) is described below. Examples of the compound represented by Formula (I) include embodiments having all combinations of specific examples given below.

As for the ring A, the ring A is a C5-C7 non-aromatic carbocycle (e.g., cyclopentane, cyclohexane, cycloheptane, etc.) or a 5- to 7-membered non-aromatic heterocycle (e.g., tetrahydrofuran, tetrahydropyran, oxepane, pyrrolidine, piperidine, azepane, etc.), and the non-aromatic carbocycle and the non-aromatic heterocycle may be further fused with a benzene ring, a 3- to 7-membered non-aromatic carbocycle (e.g., cyclopropane, cyclopentane, etc.) or a 3- to 7-membered non-aromatic heterocycle (e.g., tetrahydrofuran, etc.) and may form a spiro ring of a 3- to 7-membered non-aromatic carbocycle (e.g., cyclopropane, cyclobutane, cyclopentane, etc.) and a 3- to 7-membered non-aromatic heterocycle (e.g., oxetane, tetrahydrofuran, 1,3-dioxolane, etc.).

Examples of one preferred embodiment of the ring A include a C5-C7 non-aromatic carbocycle (e.g., cyclopentane, cyclohexane, cycloheptane, etc.) and a 5- to 7-membered non-aromatic heterocycle (e.g., tetrahydrofuran, tetrahydropyran, oxepane, pyrrolidine, piperidine, azepane, etc.).

Another preferred embodiment of the ring A is a C5-C7 non-aromatic carbocycle (e.g., cyclopentane, cyclohexane, cycloheptane, etc.), and a more preferred embodiment is a C5-C6 non-aromatic carbocycle (e.g., cyclopentane, cyclohexane, etc.).

Examples of the ring B include a benzene ring and a pyridine ring.

A preferred embodiment of the ring B is a benzene ring.

Examples of $R^1$ each independently include halogen, alkyl, haloalkyl, alkyloxy, cyano, and haloalkyloxy.

One preferred embodiment of $R^1$ is halogen, alkyl, or haloalkyl.

A more preferred embodiment of $R^1$ is halogen.

Examples of $R^{2a}$ and $R^{2b}$ each independently include hydrogen, alkyl, or haloalkyl.

One preferred embodiment of each of $R^{2a}$ and $R^{2b}$ is hydrogen.

One preferred embodiment of $R^{2a}$ is hydrogen.

One preferred embodiment of $R^{2b}$ is hydrogen or methyl, and a more preferred embodiment is hydrogen.

Examples of $R^3$ include alkyl and haloalkyl.

One preferred embodiment of $R^3$ is alkyl.

Examples of $R^4$ include hydrogen and alkyl.

One preferred embodiment of $R^4$ is hydrogen or methyl, and a more preferred embodiment is hydrogen.

Examples of $R^5$ include hydrogen and alkyl.

One preferred embodiment of $R^5$ is hydrogen.

$R^6$ is each independently include halogen, alkyl, haloalkyl, alkyloxy, haloalkyloxy, or alkyloxyalkyl, or two $R^6$s bonded to a non-adjacent atom are taken together with each other to form a C1-C3 bridge which may have an intervening heteroatom ($NR^7$, O, or S).

One preferred embodiment of $R^6$ is halogen, haloalkyl, alkyloxy, haloalkyloxy, or alkyloxyalkyl, and a more preferred embodiment is alkyloxy or alkyloxyalkyl.

Another preferred embodiment of $R^6$ is halogen, C1-3 haloalkyl, C1-3 alkyloxy, C1-3 haloalkyloxy, or C1-3 alkyloxy C1-3 alkyl, and a more preferred embodiment is C1-3 alkyloxy or C1-3 alkyloxy C1-3 alkyl.

As another preferred embodiment of $R^6$, two $R^6$s bonded to a non-adjacent atom are taken together with each other to form a C1-C3 bridge.

Examples of $R^7$ include hydrogen, alkyl, haloalkyl, alkyloxyalkyl, alkylcarbonyl, alkyloxycarbonyl, carbamoyl, alkylcarbamoyl, and alkylsulfonyl.

Examples of one preferred embodiment of $R^7$ include hydrogen, C1-3 alkyl, C1-3 haloalkyl, C1-3 alkyloxy C1-3 alkyl, C1-3 alkylcarbonyl, C1-3 alkyloxycarbonyl, carbamoyl, C1-3 alkylcarbamoyl, and C1-3 alkylsulfonyl.

n includes an integer of 1 to 3.

One preferred embodiment of n is an integer of 2 or 3.

One more preferred embodiment of n is an integer of 1 or 2.

m includes an integer of 0 to 3.

One preferred embodiment of m is an integer of 1 to 3, and a more preferred embodiment is an integer of 1 or 2.

Another preferred embodiment of m is an integer of 0 to 2.

Examples of Q include —NHC(O)— (the left bond binds to $CR^{2a}R^{2b}$) and a 5-membered aromatic heterocycle, One preferred embodiment of Q is —NHC(O)—.

Another preferred embodiment of Q is a 5-membered aromatic heterocycle.

Another preferred embodiment of Q is the following rings (the left bond binds to $CR^{2a}R^{2b}$);

[Chemical Formula 12]

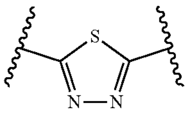
(1)

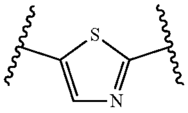
(2)

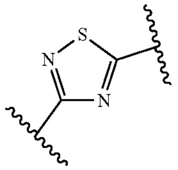
(3)

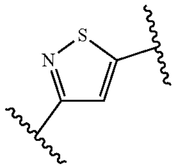
(4)

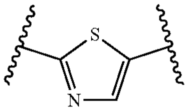
(5)

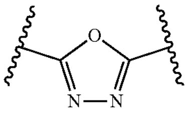
(6)

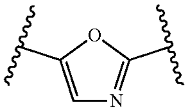
(7)

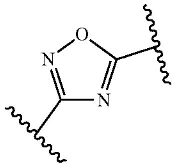
(8)

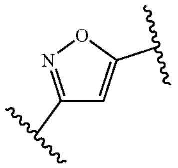
(9)

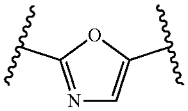
(10)

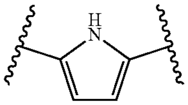
(11)

-continued (12)

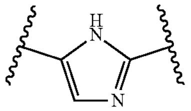

(13)

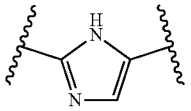

(14)

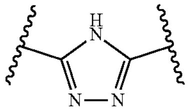

(15)

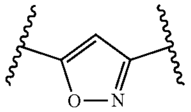

(16)

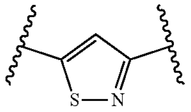

(17)

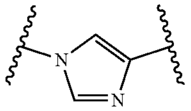

(18)

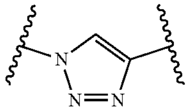

(19)

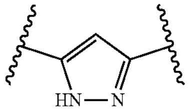

(20)

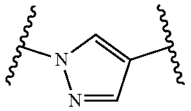

Another preferred embodiment of Q is the following rings (the left bond binds to $CR^{2a}R^{2b}$);

[Chemical Formula 13]

(1)

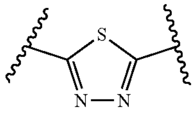

(2)

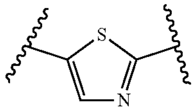

-continued (20)

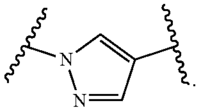

A more preferred embodiment of Q is a ring represented by the above (1).

A preferred embodiment of a stereochemistry of the carbon atom adjacent to $R^4$ and $R^5$ is as follows:

[Chemical Formula 14]

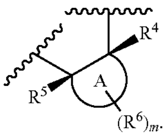

EMBODIMENT 1

A compound represented by Formula (IA):

[Chemical Formula 15]

(IA)

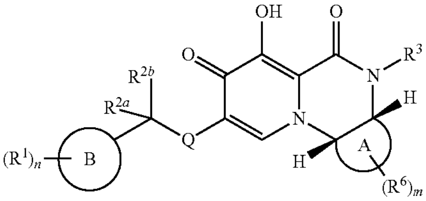

wherein ring A is a C5-C6 non-aromatic carbocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^6$s are each independently halogen, alkyl, haloalkyl, alkyloxy, haloalkyloxy, or alkyloxyalkyl; or two $R^6$s bonded to a non-adjacent atom may be taken together with each other to form a C1-C3 bridge;

n is an integer of 1 to 3; and m is an integer from 1 to 3, or a pharmaceutically acceptable salt thereof.

EMBODIMENT 2

A compound represented by Formula (IA):

[Chemical Formula 16]

(IA)

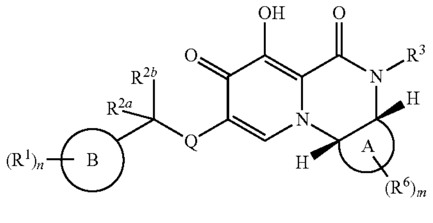

wherein ring A is a C5-C6 non-aromatic carbocycle, and the non-aromatic carbocycle is further fused with a benzene ring, a 4- to 7-membered non-aromatic carbocycle, or a 3- to 7-membered non-aromatic heterocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge;

n is an integer of 1 to 3; and m is an integer of 0 to 3, or a pharmaceutically acceptable salt thereof.

EMBODIMENT 3

A compound represented by Formula (IA):

[Chemical Formula 17]

(IA)

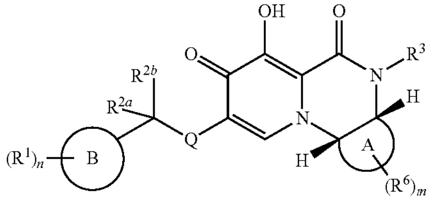

wherein ring A is a C5-C6 non-aromatic carbocycle, and the non-aromatic carbocycle further forms a spiro ring of a 3- to 7-membered non-aromatic carbocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge;

n is an integer of 1 to 3; and m is an integer of 0 to 3, or a pharmaceutically acceptable salt thereof.

EMBODIMENT 4

A compound represented by Formula (IA):

[Chemical Formula 18]

(IA)

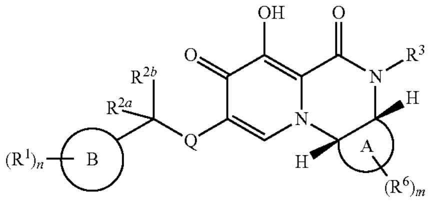

wherein ring A is a C5-C7 non-aromatic carbocycle or a 5- to 7-membered non-aromatic heterocycle, and the non-aromatic carbocycle and the non-aromatic heterocycle may be further fused with a benzene ring, a 3- to 7-membered non-aromatic carbocycle, or a 3- to 7-membered non-aromatic heterocycle and may form a spiro ring of a 3- to 7-membered non-aromatic carbocycle and a 3- to 7-membered non-aromatic heterocycle;

ring B is a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^4$ and $R^5$ are each independently hydrogen or alkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge which may have an intervening heteroatom;

n is an integer of 1 to 3; and m is an integer of 0 to 3, or a pharmaceutically acceptable salt thereof.

EMBODIMENT 5

A compound represented by Formula (IA):

[Chemical Formula 19]

(IA)

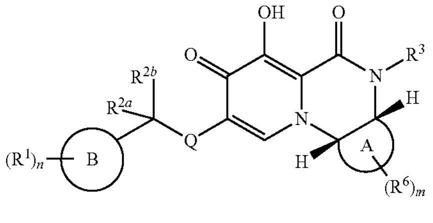

wherein ring A is a C5-C7 non-aromatic carbocycle or a 6- to 7-membered non-aromatic heterocycle, and the non-aromatic carbocycle and the non-aromatic heterocycle may be further fused with a benzene ring, a 3- to 7-membered non-aromatic carbocycle, or a 3- to 7-membered non-aromatic heterocycle and may form a spiro ring of a 3- to 7-membered non-aromatic carbocycle and a 3- to 7-membered non-aromatic heterocycle;

ring B is a benzene ring or a pyridine ring;

Q is a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^4$ and $R^5$ are each independently hydrogen or alkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge which may have an intervening heteroatom;

n is an integer of 1 to 3; and m is an integer of 0 to 3, or a pharmaceutically acceptable salt thereof.

EMBODIMENT 6

A compound represented by Formula (IA):

[Chemical Formula 20]

(IA)

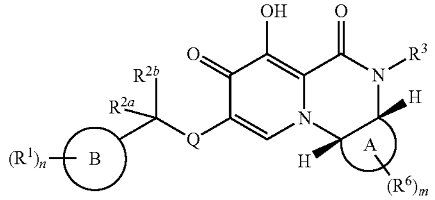

wherein ring A is a 5- to 6-membered non-aromatic heterocycle, and the non-aromatic heterocycle is further fused with a benzene ring, a 3- to 7-membered non-aromatic carbocycle, or a 3- to 7-membered non-aromatic heterocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge;

n is an integer of 1 to 3; and m is an integer of 0 to 3, or a pharmaceutically acceptable salt thereof.

EMBODIMENT 7

A compound represented by Formula (IA):

[Chemical Formula 21]

(IA)

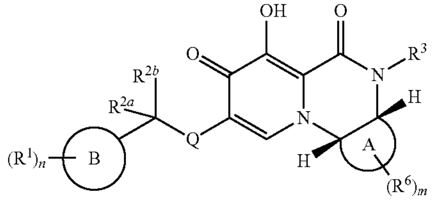

wherein ring A is a 5- to 6-membered non-aromatic heterocycle, and the non-aromatic heterocycle further forms a spiro ring of a 3- to 7-membered non-aromatic carbocycle and a 3- to 7-membered non-aromatic heterocycle;

ring B is a benzene ring or a pyridine ring;

Q is —NHC(O)— (the left bond binds to $CR^{2a}R^{2b}$) or a 5-membered aromatic heterocycle;

$R^1$ is each independently halogen, alkyl, haloalkyl, alkyloxy, cyano, or haloalkyloxy;

$R^{2a}$ and $R^{2b}$ are each independently hydrogen, alkyl, or haloalkyl;

$R^3$ is alkyl or haloalkyl;

$R^6$ is each independently halogen, alkyl, haloalkyl, alkyloxy, haloalkyloxy, or alkyloxyalkyl; or two $R^6$s bonded to a non-adjacent atom may be taken together with each other to form a C1-C3 bridge;

n is an integer of 1 to 3; and m is an integer of 0 to 3, or a pharmaceutically acceptable salt thereof.

A feature of the compound of the present invention is that ring A in Formula (I) is fixed to a specific conformation to attain excellent resistance profile, in vivo kinetics and safety. Another feature of the compound of the present invention is that an optically active tricyclic or more pyridopyrazine derivative is obtained in Formula (I) to attain excellent resistance profile, in vivo kinetics and safety.

The compound of the present invention is not limited to a specific isomer and includes all possible isomers (e.g., keto-enol isomers, imine-enamine isomers, diastereomers, optical isomers, and rotational isomers), racemates or mixtures thereof, unless otherwise specified.

Examples of the pharmaceutically acceptable salt of the compound of the present invention include salts of the compound of the present invention with alkaline metals (e.g., lithium, sodium, and potassium), alkaline earth metals (e.g., calcium and barium), magnesium, transition metals (e.g., zinc and iron), ammonia, organic bases (e.g., trimethylamine, triethylamine, dicyclohexylamine, ethanolamine, triethanolamine, meglumine, diethanolamine, ethylenediamine, pyridine, picoline, and quinoline) and amino acids, and salts of the compound of the present invention with inorganic acids (e.g., hydrochloric acid, sulfuric acid, nitric acid, carbonic acid, hydrobromic acid, phosphoric acid, and hydroiodic acid) and organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, and ethanesulfonic acid). These salts can be formed by a conventional method.

The compound of the present invention or its pharmaceutically acceptable salt may form a solvate (e.g., a hydrate), cocrystals and/or a crystal polymorph. The present invention also encompasses such various solvates, cocrystals and crystal polymorphs. "Solvates" may be those wherein any numbers of solvent molecules (e.g., water molecules or the like) are coordinated with the compounds of the present invention. When the compounds of the present invention or its pharmaceutically acceptable salts are allowed to stand in the atmosphere, the compounds may absorb water, resulting in attachment of adsorbed water or formation of hydrates. Recrystallization of the compounds of the present invention or its pharmaceutically acceptable salts may produce crystal polymorphs. "Cocrystal" means that the compound of the present invention or salt thereof and a counter molecule are present in the same crystal lattice, and a cocrystal with any number of counter molecules may be formed.

The compound of the present invention or its pharmaceutically acceptable salt may form a prodrug. The present invention also encompasses such various prodrugs. The prodrug is a derivative of the compound of the present invention having a chemically or metabolically decomposable group, and is a compound that becomes the pharmaceutically active compound of the present invention by solvolysis or under physiological conditions in vivo. The prodrug includes, for example, a compound that is converted to the compound represented by Formula (I) through enzymatic oxidation, reduction, hydrolysis, or the like under physiological conditions in vivo, and a compound that is converted to the compound represented by Formula (I) through hydrolysis by gastric juice or the like. Methods for selecting and producing an appropriate prodrug derivative are described in, for example, "Design of Prodrugs, Elsevier, Amsterdam, 1985". The prodrug may have activity in itself.

When the compound represented by Formula (I) or its pharmaceutically acceptable salt has a hydroxyl group, examples of the prodrug include prodrugs such as acyloxy derivatives and sulfonyloxy derivatives produced by reacting the compound having a hydroxyl group with an appropriate acyl halide, an appropriate acid anhydride, an appropriate sulfonyl chloride, an appropriate sulfonyl anhydride and a mixed anhydride, or using a condensing agent. Examples thereof include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, p-$CH_3O$-$PhSO_3$—, $PhSO_3$—, and p-$CH_3PhSO_3$—.

Method for Producing Compound of Present Invention

The compound of the present invention can be produced by, for example, general synthesis methods shown below. Extraction, purification, and the like can be performed by treatment performed in usual experiments of organic chemistry.

The compound of the present invention can be synthesized with reference to an approach known in the art.

(Process 1)

[Chemical Formula 22]

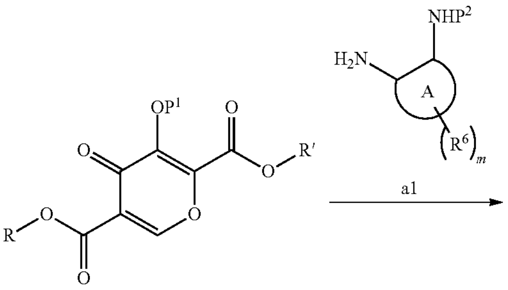

a

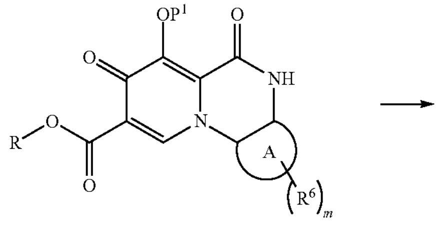

a2

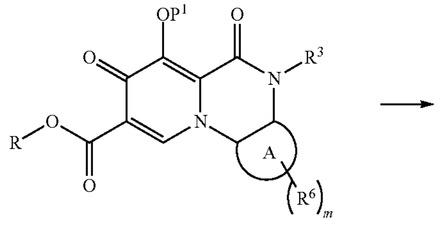

a3

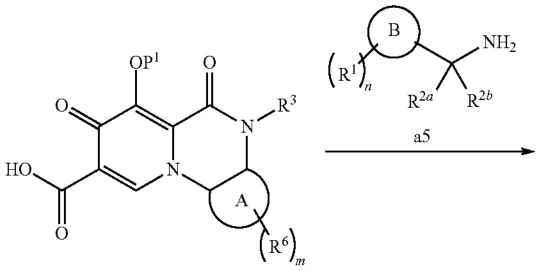

a4

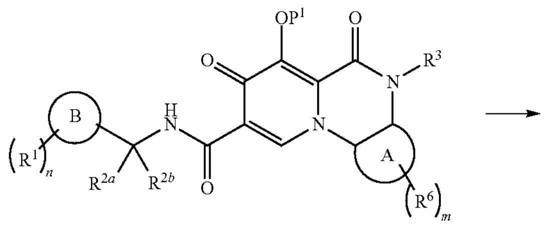

a6

-continued

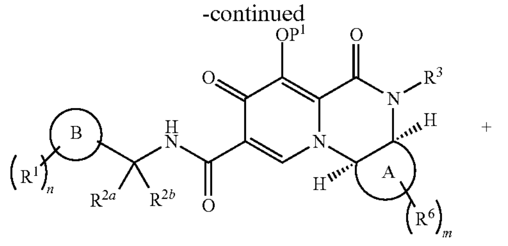

a7

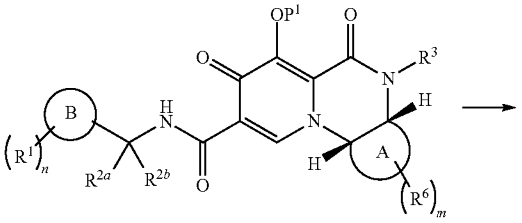

a8

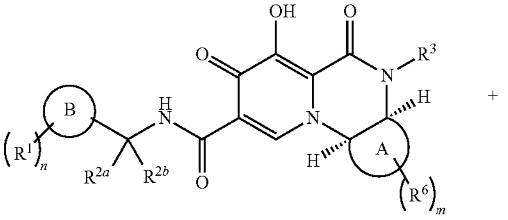

a9

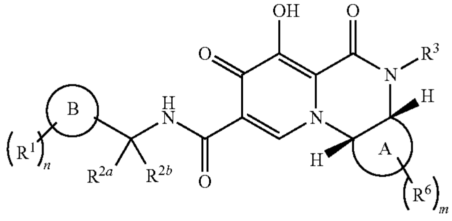

a10 wherein $P^1$ is a hydroxy-protecting group; $P^2$ is an amino-protecting group; each of R and R' is a carboxy-protecting group; each of $P^1$, $P^2$, R, and R' may be a group that can be protected and/or deprotected by a method described in, for example, Protective Groups in Organic Synthesis, Theodora W Greene (John Wiley & Sons Inc.), and, for example, $P^1$ is aromatic carbocyclylalkyl or the like, $P^2$ is alkyloxycarbonyl or the like, and each of R and R' is alkyl or the like; and the other symbols are as defined above.

Step 1

Compound a1 which can be commercially available or prepared by a known method is added to compound a which can be commercially available or prepared by a known method, in the presence of a solvent such as methanol, ethanol, toluene, dioxane, THF, or water or a mixed solvent thereof and in the presence or absence of a base such as sodium bicarbonate, and the mixture is reacted at 0° C. to 80° C., preferably 20° C. to 60° C., for 0.1 hours to 24 hours, preferably 1 hour to 12 hours. Subsequently, compound a2 can be obtained by adding a base such as cesium carbonate, potassium carbonate, or DBU in the presence of a solvent such as methanol, ethanol, toluene, dioxane, or THF and reacting the mixture at 0° C. to 100° C., preferably 20° C. to 80° C., for 0.1 hours to 24 hours, preferably 1 hour to 12 hours, after the mixture is subjected to a known general deprotection reaction of amino-protecting groups.

Step 2

Compound a3 can be obtained by adding a base such as sodium carbonate, potassium carbonate, or cesium carbonate and an alkyl halide such as iodomethane or iodoethane to compound a2 in the presence of a solvent such as DMF, DMA, NMP, DMSO, or THF and reacting the mixture at 0° C. to 80° C., preferably 20° C. to 60° C., for 0.1 hours to 24 hours, preferably 1 hour to 12 hours.

Step 3

Compound a4 can be obtained by subjecting compound a3 to the general known deprotection reaction of carboxy-protecting groups.

Step 4

Compound a6 can be obtained by adding a condensing agent such as HATU, WSC·HCl, or PyBOP to compound a4 in the presence of a solvent such as DMF, DMA, NMP, THF, chloroform, or dichloromethane, adding thereto compound a5 which can be commercially available or prepared by a known method, and a base such as triethylamine, N-methylmorpholine, pyridine, or diisopropylethylamine, and reacting the mixture at 10° C. to 60° C., preferably 20° C. to 40° C., for 0.1 hours to 24 hours, preferably 1 hour to 12 hours.

Step 5

Compound a6 can be resolved into compounds a7 and a8 by chiral SFC.

Step 6

Compounds a9 and a10 can be obtained by subjecting each of compounds a7 and a8 to the general known deprotection reaction of hydroxy-protecting groups.

(Process 2)

[Chemical Formula 23]

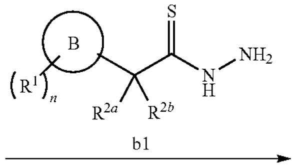

b1 a4

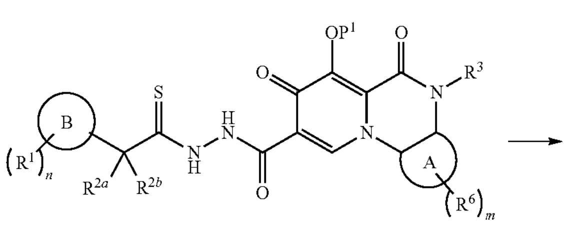

b2

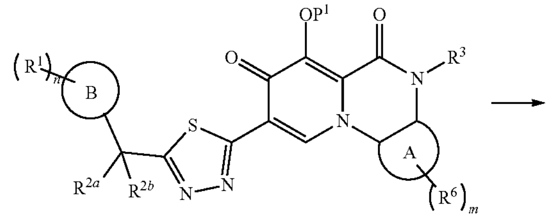

b3

-continued

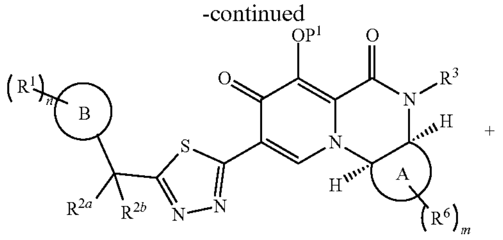

b4

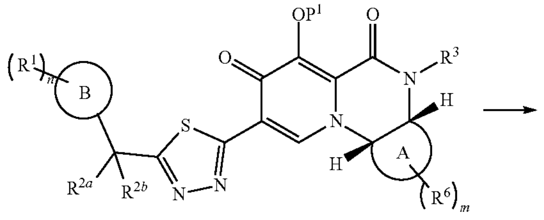

b5

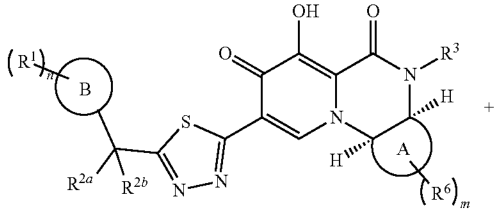

b6

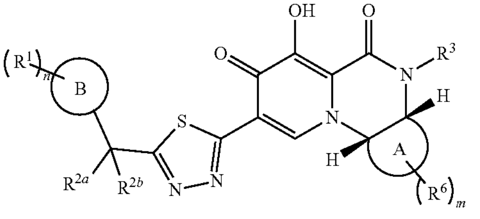

b7 wherein each symbol is as defined above.

Step 1

Compound b2 can be obtained by adding a base such as triethylamine or diisopropylethylamine and ethyl chloroformate or the like to compound a4 in the presence of a solvent such as dichloromethane, dichloroethane, chloroform, DMF, DMA, NMP, or THF to prepare a mixed acid anhydride, then adding thereto compound b1 which can be commercially available or prepared by a known method, and reacting the mixture at 0° C. to 60° C., preferably 0° C. to 20° C., for 0.1 hours to 24 hours, preferably 1 hour to 12 hours.

Step 2

Compound b3 can be obtained by acting an acid such as T3P, trifluoroacetic acid, phosphoric acid, hydrochloric acid, sulfuric acid, or hydrobromic acid on compound b2 in the presence of a solvent such as ethyl acetate, dichloromethane, dichloroethane, chloroform, dioxane, DMF, DMA, or THF, and reacting the mixture at 20° C. to 130° C., preferably 60° C. to 100° C., for 0.1 hours to 24 hours, preferably 1 hour to 12 hours.

Step 3

Compound b3 can be resolved into compounds b4 and b5 by chiral SFC.

Step 4

Compounds b6 and b7 can be obtained by subjecting each of compounds b4 and b5 to the general known deprotection reaction of hydroxy-protecting groups.

The compound of the present invention obtained above may be further chemically modified to synthesize another compound. In addition, in the above reaction, when a reactive functional group (e.g., OH, COOH, $NH_2$) is present on a side chain part, etc., the group may be protected before the reaction and may be deprotected after the reaction if desired.

Examples of protecting groups (such as an amino-protecting group, a hydroxy-protecting group, and the like) can include protecting groups, such as ethoxycarbonyl, tert-butoxycarbonyl, acetyl, benzyl, and the like, which are described in Protective Groups in Organic Synthesis, written by T. W. Greene, John Wiley & Sons Inc. (1991), or the like. Methods for the introduction and removal of a protecting group are methods commonly used in synthetic organic chemistry (see, for example, methods described in Protective Groups in Organic Synthesis, written by T. W. Greene, John Wiley & Sons Inc., (1991), or the like) or can be obtained in accordance therewith. In addition, a functional group included in each substituent can be converted by a known method (for example, those described in Comprehensive Organic Transformations, written by R. C. Larock (1989), and the like) in addition to the above production methods. Some of the compounds of the present invention can be used as a synthetic intermediate, further leading to a new derivative. Intermediates and target compounds produced in each of the above production methods can be isolated and purified by a purification method commonly used in synthetic organic chemistry, for example, subjecting them to neutralization, filtration, extraction, washing, drying, concentration, recrystallization, any kind of chromatography, or the like. In addition, intermediates can be subjected to a next reaction without further purification.

The compound of the present invention is useful, for example, as a medicament such as antiviral drug. The compound of the present invention has remarkable inhibitory activity against virus integrase. Therefore, the compound of the present invention can be expected to have a preventive or therapeutic effect on various diseases caused by a virus which produces at least integrase and increases at infection in an animal cell; and, for example, it is useful as an integrase inhibitor against retroviruses (e.g., HIV-1, HIV-2, HTLV-1, SIV, FIV, etc.); and useful as an anti-HIV drug and the like. A more preferred compound has the following characteristics as pharmacokinetics in the body: the blood concentration is high; the duration of an effect is long; the transitivity to tissue is remarkable; and/or the like. In addition, a preferred compound is safe with regard to a side effect (e.g., inhibition against CYP enzyme, mutagenicity, electrocardiogram QT interval prolongation, and arrhythmia).

In addition, the compound of the present invention may be used in a combination therapy in combination with an anti-HIV drug having the different action mechanism such as a reverse transcriptase inhibitor and/or a protease inhibiting agent, etc.

Further, the above use includes not only use as a mixture for anti-HIV, but also use as a concomitant agent for increasing the anti-HIV activity of another anti-HIV drug such as cocktail therapy and the like.

In addition, the compound of the present invention can be used to prevent infection with a retrovirus vector from spreading into a tissue other than a target tissue, upon use of a retrovirus vector based on HIV or MLV in the field of gene therapy. Particularly, when a cell or the like is infected with a vector in vitro and then returned into a body, if the compound of the present invention is administered in advance, unnecessary infection in the body can be prevented.

The pharmaceutical composition of the present invention can be administered orally or parenterally. Examples of the parenteral administration method include percutaneous administration, subcutaneous administration, intravenous administration, intraarterial administration, intramuscular administration, intraperitoneal administration, transmucosal administration, inhalation, transnasal administration, eye drops, ear drops, and intravaginal administration.

For oral administration, any dosage form usually used such as a solid preparation for internal use (e.g., tablets, powders, granules, capsules, pills, and films) or a liquid preparation for internal use (e.g., suspensions, emulsions, elixirs, syrups, lemonades, spirits, aromatic water, extracts, decoctions, and tinctures) can be prepared according to a routine method and administered. The tablets may be sugar-coated tablets, film-coated tablets, enteric coated tablets, sustained-release tablets, troche tablets, sublingual tablets, buccal tablets, chewable tablets or orally disintegrating tablets. The powders and the granules may be dry syrups. The capsules may be soft capsules, microcapsules or sustained-release capsules.

For parenteral administration, any dosage form usually used such as an injection, drops, and an external preparation (e.g., eye drops, nasal drops, ear drops, aerosols, inhalants, lotions, injectable fillers, liniments, gargles, enemas, ointments, plasters, gels, creams, patches, poultices, powders for external use, and suppositories) can be suitably administered. The injection may be an emulsion of O/W, W/O, O/W/O, W/O/W type, or the like.

An effective amount of the compound of the present invention can be mixed, if necessary, with various pharmaceutical additives, such as an excipient, a binder, a disintegrant, and a lubricant, suitable for the dosage form to prepare a pharmaceutical composition. Furthermore, the pharmaceutical composition can be prepared into a pharmaceutical composition for use for a child, an elderly, a patient with a serious case, or a surgical operation, by appropriately changing the effective amount of the compound of the present invention, the dosage form, and/or various pharmaceutical additives. For example, pediatric pharmaceutical compositions may be administered to patients who are neonates (younger than 4 weeks old after the birth), infants (4 weeks old to younger than 1 year old after the birth), children (1 year old or older and younger than 7 years old), infant children (7 years old or older and younger than 15 years old), or 15 to 18 years old. For example, the geriatric pharmaceutical compositions may be administered to patients who are 65 years old or older.

The dose of the pharmaceutical composition of the present invention is desirably set in consideration of the age or body weight of a patient, the type or severity of a disease, an administration route, etc. For oral administration, the dose is within the range of usually 0.05 to 100 mg/kg/day, preferably 0.1 to 10 mg/kg/day. Although varying depending on the administration route, the dose in the case of parenteral administration is within the range of usually 0.005 to 10 mg/kg/day and preferably 0.01 to 1 mg/kg/day. This dose can be administered once a day to once a month or once three months.

EXAMPLES

Hereinafter, Examples will be described.

Abbreviation

Bn: Benzyl
DBU: Diazabicycloundecene
DMA: Dimethylacetamide
DMF: Dimethylformamide
DMSO: Dimethylsulfoxide
HATU: O-(7-Azabenzotriazol-1-yl)-N,N,N',N'-tetramethyluronium hexafluorophosphate
NMP: N-Methylpyrrolidone
PyBOP: (Benzotriazol-1-yloxy)tripyrrolidinophosphonium hexafluorophosphate
T3P: Propylphosphonic anhydride
THF: Tetrahydrofuran
WSC·HCl: 1-Ethyl-3-(3-dimethylaminopropyl)carbodiimide hydrochloride NMR analysis obtained in each Example was conducted at 300 MHz or 400 MHz, and the measurement was performed using DMSO-$d_6$ or $CDCl_3$. NMR data indicated herein may not describe all measured peaks.

In Examples, "No." represents compound number, "Structure" means a chemical structure, "MS" represents a molecular weight in LC/MS (liquid chromatography/mass spectrometry), and the molecular weight was measured under the following conditions.

Measurement Conditions [1]

Column: Shim-pack XR-ODS (2.2 μm, i.d. 3.0×50 mm) (SHIMADZU CORPORATION)

Flow rate: 1.6 mL/min; UV detection wavelength: 254 nm;

Mobile phase: [A] is an aqueous solution containing 0.1% formic acid, and [B] is an acetonitrile solution containing 0.1% formic acid Gradient: Linear gradient of 10% to 100% solvent [B] for 3 minutes was performed, and 100% solvent [B] was maintained for 0.5 minutes.

Measurement Conditions [2]

Column: ACQUITY UPLC (registered trademark) BEH C18 (1.7 μm i.d.2.1×50 mm) (Waters)

Flow rate: 0.8 mL/min; UV detection wavelength: 254 nm;

Mobile phase: [A] is an aqueous solution containing 0.1% formic acid, and [B] is an acetonitrile solution containing 0.1% formic acid Gradient: Linear gradient of 5% to 100% solvent [B] for 3.5 minutes was performed, and then 100% solvent [B] was maintained for 0.5 minute.

Example 1

[Chemical Formula 24]

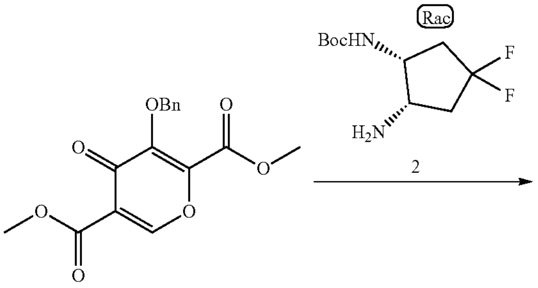

1

-continued

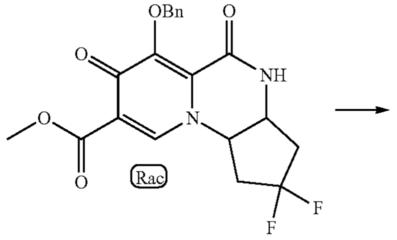

3

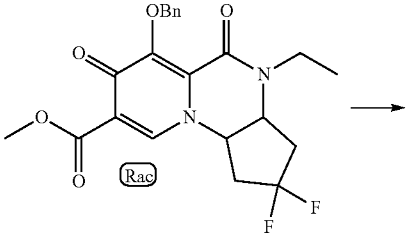

4

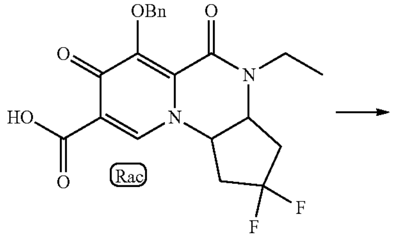

5

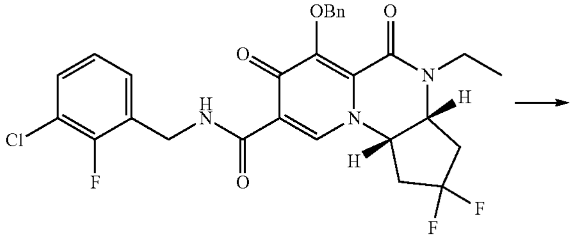

6

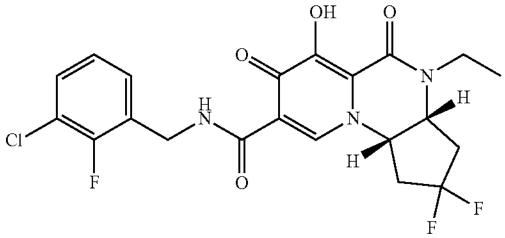

I-001 wherein Rac represents a racemate.

Step 1

Compound 1 (1.11 g, 3.49 mmol) was dissolved in methanol (22.2 mL) and water (11.1 mL), Compound 2 (906 mg, 3.84 mmol) and sodium bicarbonate (586 mg, 6.97 mmol) were added, and the mixture was stirred for 2 hours at room temperature. The solvent was distilled off under reduced pressure, followed by the extraction with ethyl acetate. The organic layer was washed with saturated saline and dried over sodium sulfate, and the solvent was distilled off. The obtained crude product was dissolved in dioxane (4.0 mL), and a 4 mol/L hydrochloric/dioxane solution (8.7 mL) was added, followed by stirring for 40 minutes. The solvent was distilled off under reduced pressure, the obtained crude product was dissolved in methanol (22.2 mL), and potassium carbonate (1.45 g, 10.5 mmol) was added, followed by stirring for 1 hour at room temperature. Water (80.0 mL) was added to the reaction solution, and the precipitated solids were collected by filtration. The obtained solids were washed with water and air-dried to obtain compound 3 (1.08 g, yield 77%).

LC/MS (ESI): 405.0 (m/z), retention time (min): 1.17, LC/MS condition: [1]

Step 2

Compound 3 (680 mg, 1.68 mmol) was dissolved in DMF (6.8 mL), ethyl iodide (393 mg, 2.52 mmol) and cesium carbonate (1.10 g, 3.36 mmol) were added, and the mixture was stirred at room temperature for 3 hours. Water was added to the reaction solution, followed by extraction with ethyl acetate. Thereby, compound 4 (890 mg) was obtained as a crude product.

LC/MS (ESI): 433.1 (m/z), retention time (min): 1.44, LC/MS condition: [1]

Step 3

Compound 4 (890 mg) was dissolved in THF (14.2 mL) and water (8.4 mL), a 4 mol/L aqueous lithium hydroxide solution (0.84 mL) was added under cooling in ice, and the mixture was stirred at room temperature for 2 hours. Dilute hydrochloric acid was added to the reaction solution, followed by the extraction with ethyl acetate, the resultant was dried over sodium sulfate, and then the solvent was distilled off. The obtained residue was purified by silica gel column chromatography (chloroform-methanol) to obtain compound 5 (563 mg, yield of step 2 80%).

LC/MS (ESI): 419.0 (m/z), retention time (min): 1.85, LC/MS condition: [1]

Step 4

Compound 5 (110 mg, 0.263 mmol) was dissolved in dichloromethane (1.1 ml), (3-chloro-2-fluorophenyl)methanamine (62.9 mg, 0.394 mmol), HATU (150 mg, 0.394 mmol), and triethylamine (72.9 μL, 0.526 mmol) were added, and the mixture was stirred at room temperature for 1.5 hours. Water was added to the reaction solution, the organic layer was separated, and the solvent was distilled off. The obtained residue was purified by silica gel column chromatography (chloroform-methanol) to obtain a racemic mixture.

LC/MS (ESI): 560.3 (m/z), retention time (min): 2.35, LC/MS condition: [1]

The obtained racemic mixture was optically resolved by SFC to obtain compound 6 (66.5 mg, yield 45%).

Column: Two CHIRALPAK IC/SFC (5 μm, i.d. 250×20 mm) were used in series.

Flow rate: 20 mL/min

UV detection wavelength: 220 nm

Analysis conditions: A compositional ratio of MeOH/CO2=80/20 was kept, and the solution was sent for 40 minutes.

Step 5

Compound 6 (66.5 mg, 0.119 mmol) was dissolved in N,N-dimethylformamide (2.0 mL), lithium chloride (200 mg, 4.72 mmol) was added, and the mixture was stirred at 90° C. for 2.0 hours. The reaction solution was made acidic with a 10% aqueous citric acid solution, followed by extraction with chloroform. Thereafter, the organic layer was separated, and the solvent was distilled off. The obtained residue was purified by reversed-phase liquid chromatography to obtain compound I-1 (55.0 mg, yield 98%).

LC/MS (ESI): 470 (m/z), retention time (min): 2.06, LC/MS condition: [2]

$^1$H-NMR (CDCl3) δ: 12.84 (s, 1H), 10.39 (t, J=5.7 Hz, 1H), 8.37 (s, 1H), 7.33-7.24 (m, 2H), 7.07-6.99 (m, 1H), 4.77-4.64 (m, 3H), 4.39-4.32 (m, 1H), 3.91-3.79 (m, 1H), 3.58-3.45 (m, 1H), 2.90-2.56 (m, 4H), 1.29 (t, J=7.2 Hz, 3H).

Example 2

[Chemical Formula 25]

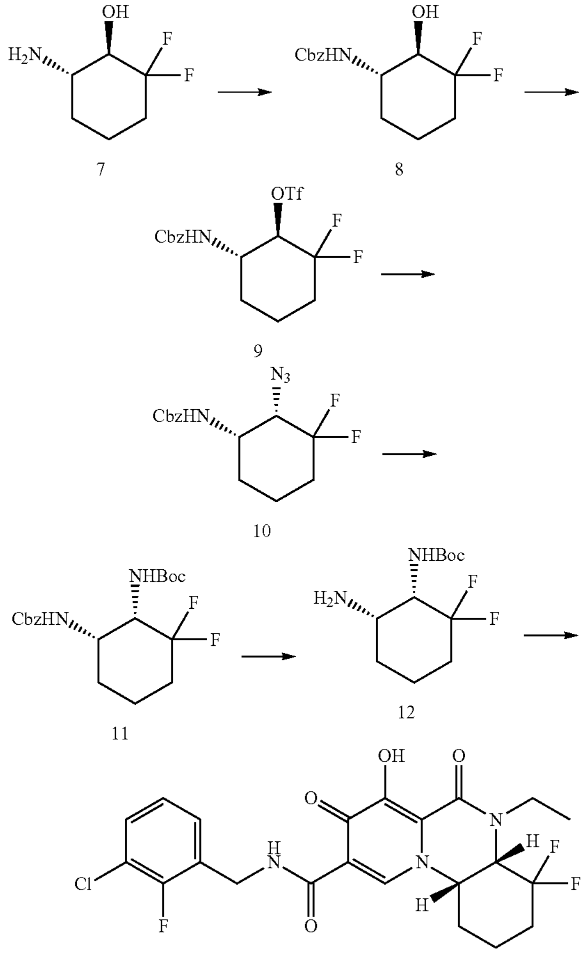

7 8 9 10 11 12 I-007

Step 1

Sodium bicarbonate (0.93 g, 11.0 mmol) and benzyl chloroformate (1.56 mL, 11.0 mmol) were added at 0° C. to an ethanol (10.0 mL) solution of compound 7 (1.11 g, 7.34 mmol) and the mixture was stirred at room temperature overnight. Purified water was added to the reaction solution, followed by the extraction with ethyl acetate, the resultant was washed with purified water and saturated saline and dried over anhydrous magnesium sulfate, and then the solvent was distilled off to obtain compound 8 (2.09 g, yield 99.8%).

$^1$H-NMR ($CDCl_3$) δ: 7.39-7.31 (m, 5H), 5.16-5.08 (m, 2H), 4.88 (brs, 1H), 3.79-3.69 (m, 1H), 3.64-3.52 (m, 1H), 2.76 (s, 1H), 2.24-2.13 (m, 1H), 2.10-2.01 (m, 1H), 1.77-1.58 (m, 3H), 1.43-1.32 (m, 1H).

Step 2

Pyridine (0.56 mL, 6.94 mmol) and anhydrous trifluoromethanesulfonic acid (1.17 mL, 6.94 mmol) were added at 0° C. to a dichloromethane (20.0 mL) solution of compound 8 (1.65 g, 5.78 mmol) and the mixture was stirred at 0° C. for 3 hours. Purified water was added to the reaction solution, followed by the extraction with dichloromethane, the resultant was washed with purified water and saturated saline and dried over anhydrous magnesium sulfate, and then the solvent was distilled off to obtain compound 9.

Step 3

Compound 9 (1.66 g, 3.97 mmol) was dissolved in NMP (15.0 mL), sodium azide (1.55 g, 23.8 mmol) was added to the solution, and the mixture was stirred at 100° C. for 1 hour. Purified water was added to the reaction solution, followed by the extraction with ethyl acetate, the resultant was washed with purified water and saturated saline and dried over anhydrous magnesium sulfate, and then the solvent was distilled off. The obtained residue was purified by silica gel chromatography to obtain compound 10 (628 mg, yield 51%).

$^1$H-NMR ($CDCl_3$) δ: 7.40-7.27 (m, 5H), 5.12 (s, 2H), 5.05-4.94 (m, 1H), 3.97 (t, J=4.1 Hz, 2H), 2.04-1.85 (m, 2H), 1.77-1.63 (m, 2H), 1.57-1.32 (m, 2H).

Step 4

Compound 10 (620 mg, 2.00 mmol) was dissolved in THF (6.2 mL), purified water (0.72 mL, 40.0 mmol) and triphenylphosphine (629 mg, 2.40 mmol) were added, and the reaction solution was stirred under refluxing with heating overnight. The reaction solution was cooled to room temperature, di-tert-butyl dicarbonate (523 mg, 0.557 mL) was added, and the mixture was stirred at room temperature for 6 hours and 45 minutes. Purified water was added to the reaction solution, followed by the extraction with ethyl acetate, the resultant was washed with purified water and saturated saline and dried over anhydrous magnesium sulfate, and then the solvent was distilled off. The obtained residue was purified by silica gel chromatography to obtain compound 11 (572 mg, 1.49 mmol).

$^1$H-NMR ($CDCl_3$) δ: 7.41-7.32 (m, 5H), 5.16-5.08 (m, 3H), 4.88 (brs, 1H), 4.28 (brs, 1H), 4.12 (q, J=7.2 Hz, 1H), 2.13 (brs, 1H), 1.88-1.60 (m, 5H), 1.45 (s, 9H).

Step 5

Compound 11 (572 mg, 1.49 mmol) was dissolved in methanol (6.0 mL), 5% palladium carbon (15.8 mg, 0.074 mmol) was added, and the mixture was stirred at room temperature under a hydrogen atmosphere for 2 hours. The insoluble matter was removed by filtration with Celite (registered trademark) and the solvent was concentrated under reduced pressure to obtain compound 12.

Step 6

Compound I-7 was obtained using compound 12 by using the same method as in Example 1.

$^1$H-NMR ($CDCl_3$) δ: 12.54 (brs, 1H), 10.48 (t, J=5.6 Hz, 1H), 8.41 (s, 1H), 7.33-7.27 (m, 2H), 7.03 (t, J=8.4 Hz, 1H), 4.73-4.65 (m, 2H), 4.62-4.57 (m, 1H), 4.22 (td, J=14.3, 7.2 Hz, 1H), 3.87 (dt, J=21.6, 2.6 Hz, 1H), 3.34 (td, J=14.1, 7.0 Hz, 1H), 2.87 (d, J=16.1 Hz, 1H), 2.41-2.30 (m, 1H), 2.06-1.79 (m, 4H), 1.32 (t, J=7.2 Hz, 3H).

LC/MS (ESI): 484 (m/z), retention time (min): 2.12, LC/MS condition: [2]

Example 3

[Chemical Formula 26]

1
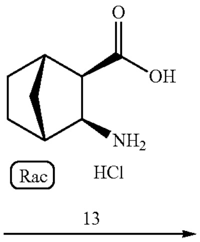

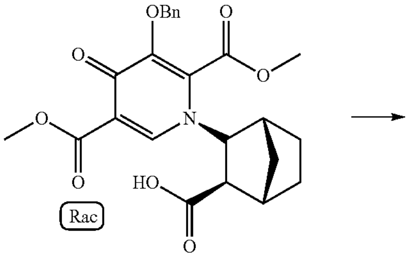

14

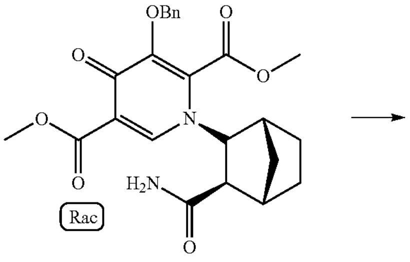

15

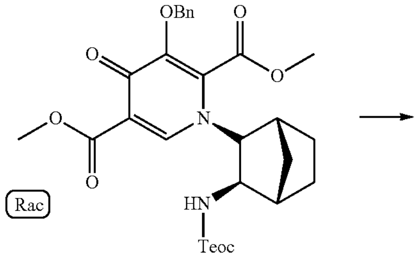

16

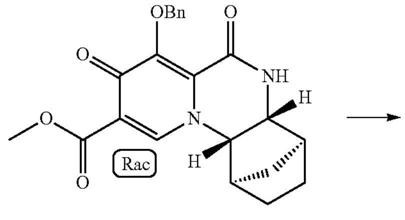

17

-continued

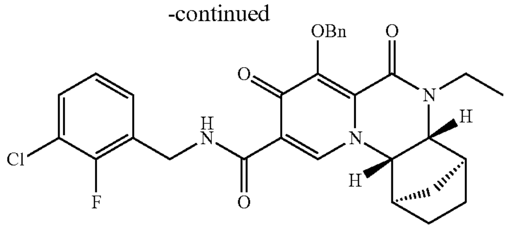

I-009

Step 1

Compound 1 (1.46 g, 4.60 mmol) was dissolved in methanol (19.4 mL), compound 13 (970 mg, 5.06 mmol) and sodium bicarbonate (812 mg, 9.66 mmol) were added, and the mixture was stirred for 3 hours at room temperature. The solvent was distilled off under reduced pressure, and then a 4 mol/L hydrochloric/dioxane solution (5.8 mL) was added, followed by stirring for 1 hour at room temperature. Water and dichloromethane were added to the reaction solution, followed by the extraction with dichloromethane, the resultant was dried over sodium sulfate, and then the solvent was distilled off. The obtained residue was suspended and filtered from a mixed solution of ethyl acetate/diisopropylether, and the obtained solids were washed with diisopropylether and dried to obtain compound 14 (1.55 g, yield 74%).

LC/MS (ESI): 456 (m/z), retention time (min): 1.79, LC/MS condition: [2]

Step 2

Compound 14 (100 mg, 0.22 mmol) was dissolved in dichloromethane (2.0 mL), triethylamine (44.4 mg, 0.44 mmol) and ethyl chloroformate (26.2 mg, 0.242 mmol) were added, and the mixture was stirred at room temperature for 1 hour. A 7 mol/L ammonia/methanol solution (0.031 mL) was added to the reaction solution, and the mixture was further stirred at room temperature for 2 hours. Dichloromethane and water were added to the reaction solution, followed by the extraction with dichloromethane, the resultant was dried over sodium sulfate, and then the solvent was distilled off to obtain compound 15.

LC/MS (ESI): 455 (m/z), retention time (min): 1.66, LC/MS condition: [2]

Step 3

Compound 15 was dissolved in dichloroethane (2.0 mL), 2-trimethylsilyl ethanol (78.0 mg, 0.66 mmol) and iodobenzene diacetate (85.0 mg, 0.264 mmol) were added to the solution, and the mixture was stirred at 80° C. for 1 hour. After the reaction solution was allowed to cool to room temperature, saturated aqueous sodium bicarbonate and a saturated aqueous sodium thiosulfate solution were added, followed by the extraction with dichloromethane, the resultant was dried over sodium sulfate, and then the solvent was distilled off to obtain compound 16.

LC/MS (ESI): 571 (m/z), retention time (min): 1.47, LC/MS condition: [2]

Step 4

Compound 16 was dissolved in THF (1.0 mL), and a 1 mol/L tetrabutylammonium fluoride/THF solution (0.44 mL), and the mixture was stirred at room temperature overnight. The reaction solution was concentrated. The obtained residue was purified by silica gel column chromatography (chloroform-methanol) to obtain compound 17 (67 mg, yield 77%).

LC/MS (ESI): 395 (m/z), retention time (min): 1.43, LC/MS condition: [2]

Step 5

Compound I-9 was synthesized in the same manner as in Example 1 by using compound 17.

$^1$H-NMR ($CDCl_3$) δ: 13.12 (s, 1H), 10.57 (t, J=5.6 Hz, 1H), 8.36 (s, 1H), 7.33-7.27 (m, 2H), 7.03 (t, J=7.9 Hz, 1H), 4.77-4.66 (m, 2H), 4.24 (d, J=8.0 Hz, 1H), 4.03 (td, J=14.1, 7.0 Hz, 1H), 3.78 (d, J=7.3 Hz, 1H), 3.25 (td, J=14.0, 7.0 Hz, 1H), 2.62 (brs, 2H), 1.83-1.13 (m, 9H).

LC/MS (ESI): 460 (m/z), retention time (min): 2.05, LC/MS condition: [2]

Example 4

[Chemical Formula 27]

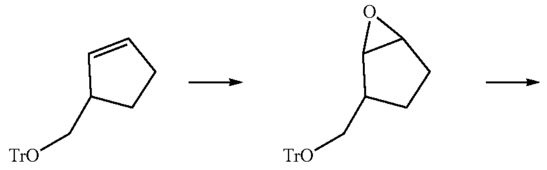

18 19

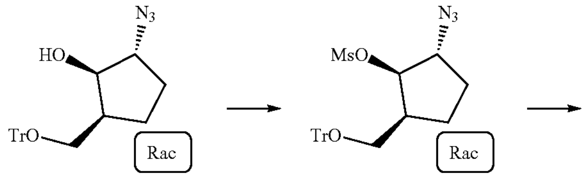

20 21

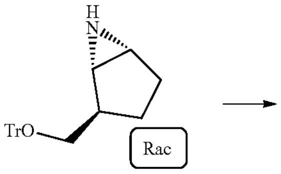

22

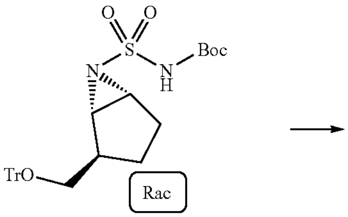

23

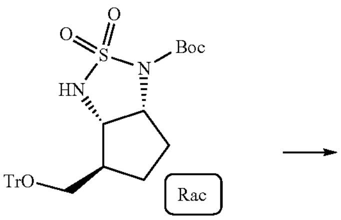

24

-continued

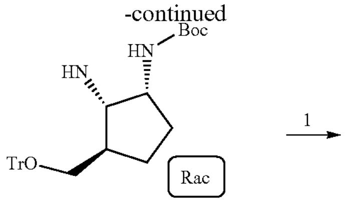

25

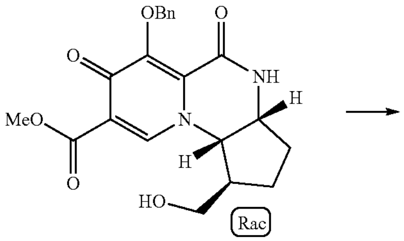

26

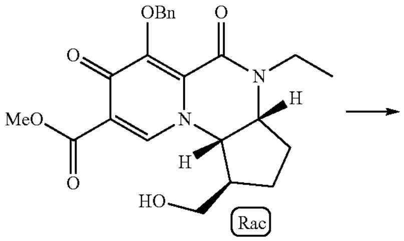

27

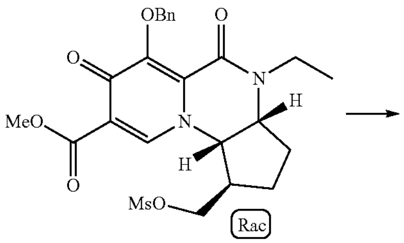

28

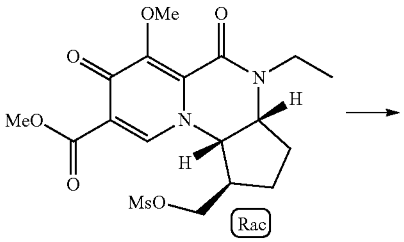

29

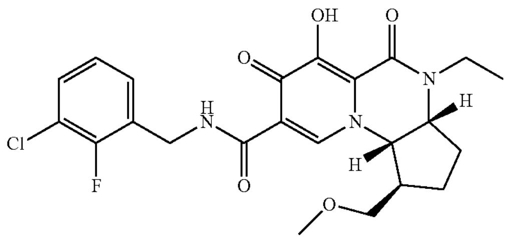

I-013

Step 1

Sodium bicarbonate (855 mg, 10.18 mmol) and metachloroperbenzoic acid (2.21 g, 8.82 mmol) were added to a dichloromethane (46 mL) solution of compound 18 (2.31 g, 6.78 mmol) and the mixture was stirred at room temperature for 2 hours. Water was added to the reaction solution, followed by extraction with chloroform. The organic layer was washed with saturated saline and dried over sodium sulfate, and the solvent was distilled off. The obtained residue was purified by silica gel column chromatography (hexane-ethyl acetate) to obtain compound 19 (2.41 g, yield 100%).

LC/MS (ESI): 378.90(m/z), retention time (min): 2.90, LC/MS condition: [1]

Step 2

Compound 19 (6.07 g, 17.03 mmol), ammonium chloride (0.911 g, 17.03 mmol), and sodium azide (5.54 g, 85 mmol) were dissolved in ethanol (61 mL) and water (12 mL) and the mixture was heated to reflux overnight. Water was added to the reaction solution, followed by extraction with ethyl acetate. The organic layer was washed with saturated saline and dried over sodium sulfate, and the solvent was distilled off. The obtained residue was purified by silica gel column chromatography (hexane-ethyl acetate) to obtain compound 20 (2.04 g, yield 30%).

LC/MS (ESI): 422.10 (m/z), retention time (min): 2.90, LC/MS condition: [2]

Step 3

Methanesulfonyl chloride (267 mg, 2.34 mmol) and triethylamine (0.33 mL, 2.33 mmol) were added to a dichloromethane (9 mL) solution of compound 20 (0.93 g, 2.33 mmol) and the mixture was stirred at room temperature overnight. A 1 mol/L aqueous solution of hydrochloric acid was added to the reaction solution, followed by the extraction with ethyl acetate. The obtained organic layer was washed with saturated saline, and then dried over sodium sulfate, and the solvent was distilled off under reduced pressure. The obtained residue was purified by silica gel column chromatography (chloroform-methanol) to obtain compound 21 (1.11 g, yield 100%).

LC/MS (ESI): 500.00 (m/z), retention time (min): 2.96, LC/MS condition: [2]

Step 4

Triphenylphosphine (665 mg, 2.53 mmol) was added to a THF (11 mL) solution of compound 21 (1.10 g, 2.30 mmol) and the mixture was stirred at room temperature for 2 hours. Water (1.1 mL) and triethylamine (0.64 mL, 4.61 mmol) were added to the reaction solution and the mixture was further stirred overnight. A saturated aqueous ammonium chloride solution was added to the reaction solution, followed by the extraction with ethyl acetate. The organic layer was washed with saturated saline and dried over sodium sulfate, and the solvent was distilled off. The obtained residue was purified by silica gel column chromatography (hexane-ethyl acetate) to obtain compound 22 (619 mg, yield 76%).

LC/MS (ESI): 356.00 (m/z), retention time (min): 1.84, LC/MS condition: [2]

Step 5 t-Butyl alcohol (0.184 mL, 1.94 mmol) was added dropwise to a toluene (6 mL) solution of chlorosulfonyl isocyanate (0.17 mL, 1.94 mmol) under cooling in ice. Subsequently, pyridine (0.34 mL, 4.26 mmol) was added dropwise to the reaction solution and the mixture was stirred for 40 minutes. A THF (6 mL) solution of compound 22 (619 mg, 1.74 mmol) was added dropwise to the reaction solution and then the mixture was stirred at room temperature overnight. A saturated aqueous ammonium chloride solution was added to the reaction solution, followed by the extraction with ethyl acetate. The organic layer was washed with saturated saline and dried over sodium sulfate, and the solvent was distilled off. The obtained residue was purified by silica gel column chromatography (hexane-ethyl acetate) to obtain compound 23 (0.61 g, yield 59%).

LC/MS (ESI): 557.10 (m/z), retention time (min): 2.96, LC/MS condition: [2]

Step 6

Compound 23 (1.91 g, 3.57 mmol) and sodium iodide (1.93 g, 12.9 mmol) were added to DMF (19 mL) and the mixture was stirred under heating at 80° C. for 1 hour. Water was added to the reaction solution, followed by extraction with ethyl acetate. The organic layer was washed with saturated saline and dried over sodium sulfate, and the solvent was distilled off to obtain compound 24 (1.91 g).

LC/MS (ESI): 557.10 (m/z), retention time (min): 2.99, LC/MS condition: [2]

Step 7

Compound 24 (510 mg, 0.954 mmol) was added to a mixed solution of pyridine (5 mL) and water (0.5 mL) and the mixture was stirred under heating at 80° C. for 1 hour. Water was added to the reaction solution, followed by extraction with ethyl acetate. The organic layer was washed with saturated saline and dried over sodium sulfate, and the solvent was distilled off. The obtained residue was purified by amino column chromatography (hexane-ethyl acetate) to obtain compound 25 (450 mg, yield 100%).

LC/MS (ESI): 473.10 (m/z), retention time (min): 2.06, LC/MS condition: [2]

Step 8

Compound 1 (310 mg, 0.973 mmol) and compound 25 (460 mg, 0.973 mmol) were dissolved in methanol (5 mL) and the mixture was stirred at room temperature overnight. The reaction solution was concentrated and then dissolved in dioxane (4.6 mL), a 4 mol/L hydrochloric/dioxane solution (3.7 mL) was added, and the mixture was stirred at room temperature for 1 hour. After the reaction solution was concentrated, THF (5 mL) and triethylamine (1.4 mL, 9.73 mmol) were added thereto and the mixture was stirred for 1 hour. The reaction solution was concentrated. The obtained residue was purified by reverse-phase column chromatography (water-acetonitrile) to obtain compound 26 (638 mg, yield 74%).

LC/MS (ESI): 399.00 (m/z), retention time (min): 1.08, LC/MS condition: [2]

Step 9

Compound 26 (293 mg, 0.735 mmol) was dissolved in DMF (2.9 mL), ethyl iodide (119 μL, 1.47 mmol) and cesium carbonate (479 mg, 1.47 mmol) were added, and the mixture was stirred at room temperature for 1 hour. The reaction solution was filtered through Celite (registered trademark) and concentrated. The obtained residue was purified by reverse-phase column chromatography (water-acetonitrile) to obtain compound 27 (157 mg, yield 50%).

LC/MS (ESI): 427.10 (m/z), retention time (min): 1.45, LC/MS condition: [2]

Step 10

Compound 27 (122 mg, 0.286 mmol) was dissolved in dichloromethane (0.5 mL), methanesulfonyl chloride (0.029 mL, 0.372 mmol) and triethylamine (0.079 mL, 0.572 mmol) were added, and the mixture was stirred at room temperature for 1 hour. A saturated aqueous solution of sodium bicarbonate was added to the reaction solution, followed by extraction with chloroform. The organic layer was washed with saturated saline and dried over sodium sulfate, and the solvent was distilled off. The obtained solid matters were washed with ethyl acetate and then dried to obtain compound 28 (122 mg, yield 85%).

LC/MS (ESI): 505.10 (m/z), retention time (min): 1.57, LC/MS condition: [2]

Step 11

Sodium methoxide (0.1 mol/L, 725 μL, 0.725 mmol) was added to a DMF(2.4 mL) solution of compound 28 (122 mg, 0.242 mmol), the mixture was stirred under heating at 80° C. for 30 minutes, acetic acid (42 μL, 0.725 mmol) was added thereto, and the solvent was distilled off. The obtained residue was purified by reverse-phase column chromatography (water-acetonitrile) to obtain compound 29 (62 mg, yield 70%).

LC/MS (ESI): 365.05 (m/z), retention time (min): 1.20, LC/MS condition: [2]

Step 12

Compound I-13 was synthesized in the same manner as in Example 1 by using compound 29.

LC/MS (ESI): 478.10 (m/z), retention time (min): 1.98, LC/MS condition: [2]

$^1$H-NMR ($CDCl_3$) δ: 12.89 (s, 1H), 10.55 (s, 1H), 8.36 (s, 1H), 7.31-7.29 (m, 1H), 7.18-7.17 (m, 1H), 7.04-7.02 (m, 1H), 4.80-4.65 (m, 2H), 4.46 (dd, J=8.2, 5.3 Hz, 1H), 4.25-4.15 (m, 1H), 3.83 (dq, J=14.0, 7.0 Hz, 1H), 3.48 (dq, J=14.0, 7.0 Hz, 1H), 3.41 (s, 3H), 3.43-3.40 (m, 2H), 2.45-2.35 (m, 1H), 2.25-2.10 (m, 1H), 2.15-1.95 (m, 2H), 1.81-1.71 (m, 1H), J=7.2 Hz, 3H).

Example 5

[Chemical Formula 28]

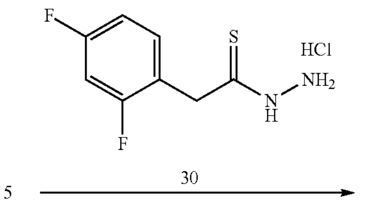

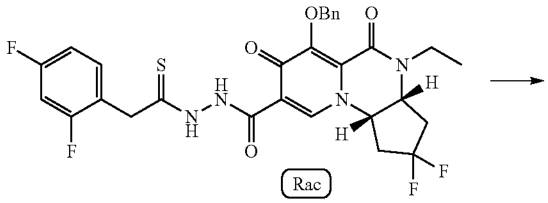

31

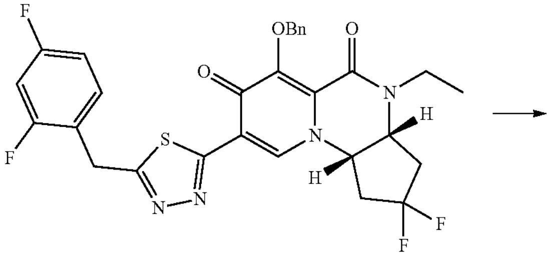

32

-continued

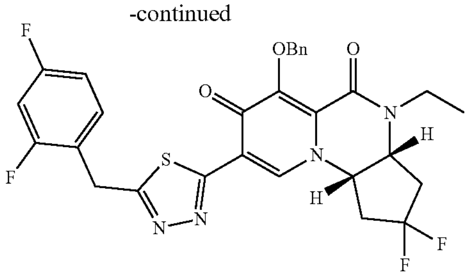

I-016

Step 1

Compound 5 (120 mg, 0.287 mmol) was dissolved in dichloromethane (2.4 mL), triethylamine (159 μL, 1.15 mmol) and ethyl chloroformate (30.3 μL, 0.315 mmol) was added under cooling in ice, and the mixture was stirred for 20 minutes. Compound 30 (82.0 mg, 0.344 mmol) was added to the reaction solution and the mixture was stirred for 1.0 hour. Water was added to the reaction solution, followed by extraction with chloroform. The solvent was distilled off to obtain compound 31 (197 mg) as a crude product of the racemic mixture.

LC/MS (ESI): 603 (m/z), retention time (min): 2.25, LC/MS condition: [1]

Step 2

Compound 31 (197 mg) was dissolved in ethyl acetate (1.2 mL), a 50% T3P/ethyl acetate solution (1.71 ml, 2.87 mmol) was added, and the mixture was heated and stirred at 80° C. for 40 minutes. Water was added to the reaction solution, followed by extraction with chloroform. Thereafter, the solvent was distilled off. The obtained residue was purified by silica gel column chromatography (hexane-ethyl acetate) to obtain a racemic mixture.

LC/MS (ESI): 585 (m/z), retention time (min): 2.30, LC/MS condition: [1]

The obtained racemic mixture was optically resolved by the same method as in Example 1 to obtain compound 32 (69.4 mg, yield 47%).

Step 3

Compound I-16 was synthesized in the same manner as in Example 1 by using compound 32.

1H-NMR ($CDCl_3$) δ: 12.88 (s, 1H), 8.60 (s, 1H), 7.35-7.24 (m, 1H), 6.90-6.81 (m, 2H), 4.83-4.72 (m, 1H), 4.50-4.37 (m, 3H), 3.92-3.80 (m, 1H), 3.60-3.45 (m, 1H), 2.96-2.55 (m, 4H), 1.31 (t, J=7.3 Hz, 3H).

LC/MS (ESI): 495 (m/z), retention time (min): 2.01, LC/MS condition: [1]

The following compounds were also synthesized in the same manner by using the general synthesis method described above or the synthesis method described in Examples.

TABLE 1

| No. | Structure |
|---|---|
| I-002 | 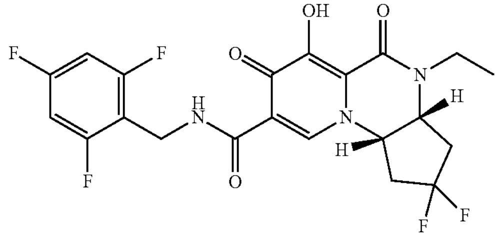 [SMILES: CCN1C(=O)c2c(O)c(=O)c(C(=O)NCc3c(F)cc(F)cc3F)cn2[C@H]2CC(F)(F)C[C@H]21] |

TABLE 1-continued
| No. | Structure |
|---|---|
| I-003 | 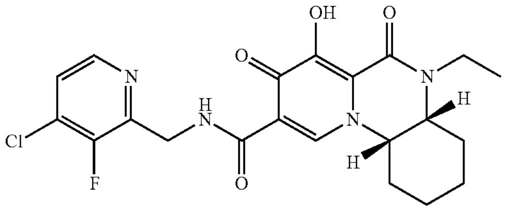 [SMILES: CCN1C(=O)c2c(O)c(=O)c(C(=O)NCc3nccc(Cl)c3F)cn2[C@H]2CCCC[C@H]21] |
| I-004 | 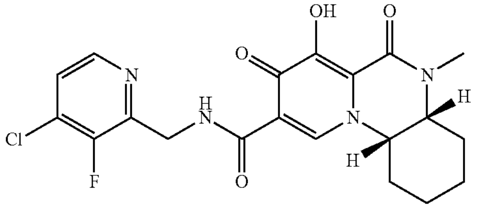 [SMILES: CN1C(=O)c2c(O)c(=O)c(C(=O)NCc3nccc(Cl)c3F)cn2[C@H]2CCCC[C@H]21] |
| I-005 | 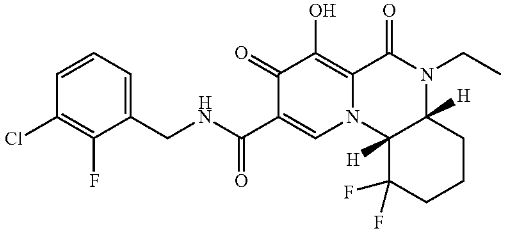 [SMILES: CCN1C(=O)c2c(O)c(=O)c(C(=O)NCc3cccc(Cl)c3F)cn2[C@@H]2[C@H]1CCCC2(F)F] |
| I-006 | 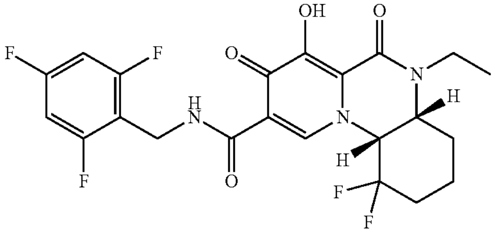 [SMILES: CCN1C(=O)c2c(O)c(=O)c(C(=O)NCc3c(F)cc(F)cc3F)cn2[C@@H]2[C@H]1CCCC2(F)F] |
| I-008 | 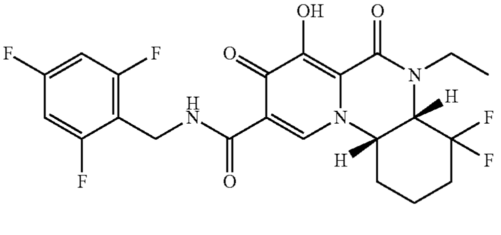 [SMILES: CCN1C(=O)c2c(O)c(=O)c(C(=O)NCc3c(F)cc(F)cc3F)cn2[C@H]2CCCC(F)(F)[C@H]21] |
| I-010 | 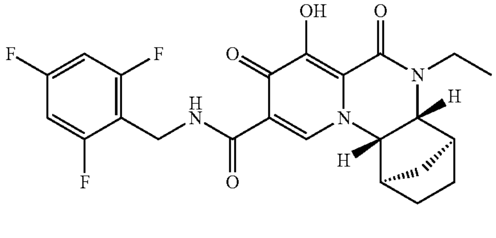 [SMILES: CCN1C(=O)c2c(O)c(=O)c(C(=O)NCc3c(F)cc(F)cc3F)cn2[C@H]2[C@@H]3CC[C@@H](C3)[C@H]21] |
TABLE 1-continued
| No. | Structure |
|---|---|
| I-011 | 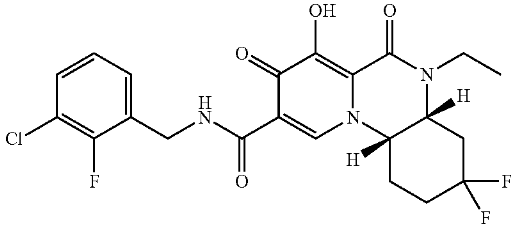 [SMILES: CCN1C(=O)c2c(O)c(=O)c(C(=O)NCc3cccc(Cl)c3F)cn2[C@H]2CCC(F)(F)C[C@H]21] |
| I-012 | 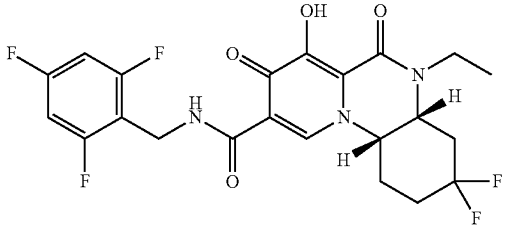 [SMILES: CCN1C(=O)c2c(O)c(=O)c(C(=O)NCc3c(F)cc(F)cc3F)cn2[C@H]2CCC(F)(F)C[C@H]21] |
| I-014 | 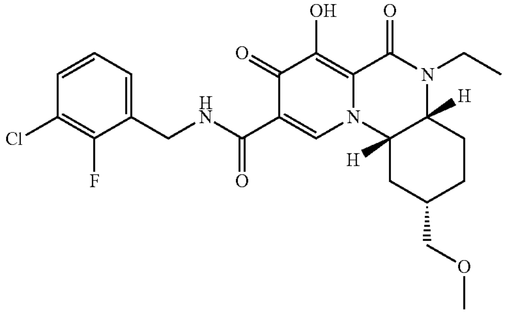 [SMILES: CCN1C(=O)c2c(O)c(=O)c(C(=O)NCc3cccc(Cl)c3F)cn2[C@H]2C[C@@H](COC)CC[C@H]21] |
| I-015 | 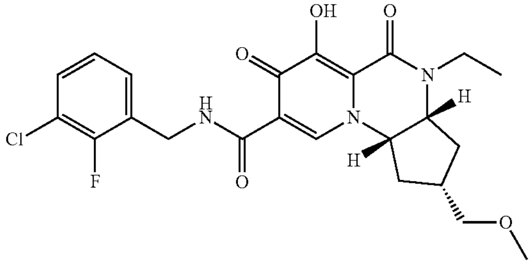 [SMILES: CCN1C(=O)c2c(O)c(=O)c(C(=O)NCc3cccc(Cl)c3F)cn2[C@H]2C[C@@H](COC)C[C@H]21] |
| I-017 | 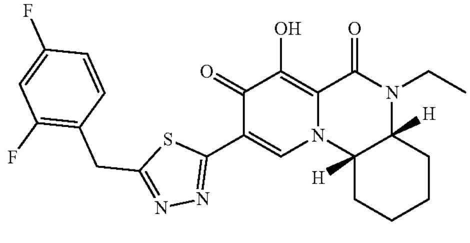 [SMILES: CCN1C(=O)c2c(O)c(=O)c(-c3nnc(Cc4ccc(F)cc4F)s3)cn2[C@H]2CCCC[C@H]21] |
| I-018 | 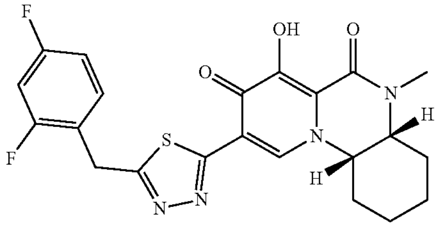 [SMILES: CN1C(=O)c2c(O)c(=O)c(-c3nnc(Cc4ccc(F)cc4F)s3)cn2[C@H]2CCCC[C@H]21] |

TABLE 1-continued
| No. | Structure |
|---|---|
| I-019 | 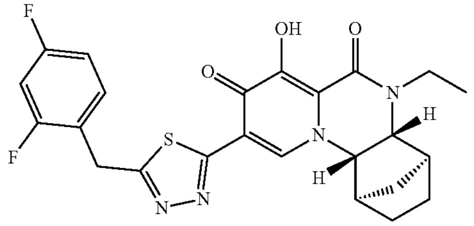 [SMILES: CCN1C(=O)c2c(O)c(=O)c(-c3nnc(Cc4ccc(F)cc4F)s3)cn2[C@H]2[C@@H]3CC[C@@H](C3)[C@H]21] |
| I-020 | 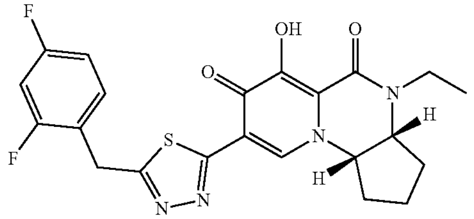 [SMILES: CCN1C(=O)c2c(O)c(=O)c(-c3nnc(Cc4ccc(F)cc4F)s3)cn2[C@H]2CCC[C@H]21] |
| I-021 | 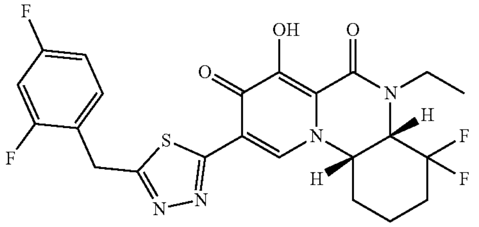 [SMILES: CCN1C(=O)c2c(O)c(=O)c(-c3nnc(Cc4ccc(F)cc4F)s3)cn2[C@H]2CCCC(F)(F)[C@H]21] |
TABLE 2
| No. | Structure |
|---|---|
| I-022 | 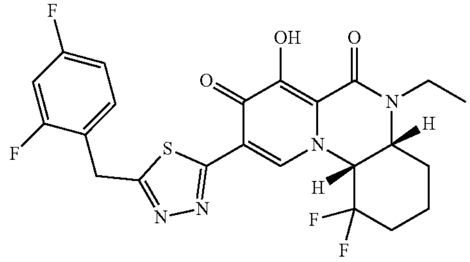 [SMILES: CCN1C(=O)c2c(O)c(=O)c(-c3nnc(Cc4ccc(F)cc4F)s3)cn2[C@@H]2[C@H]1CCCC2(F)F] |
| I-023 | 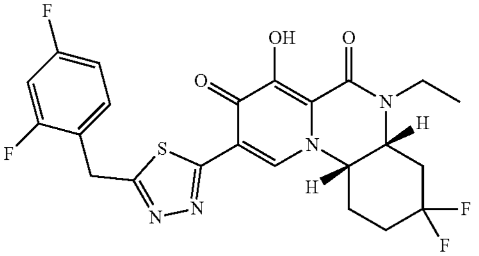 [SMILES: CCN1C(=O)c2c(O)c(=O)c(-c3nnc(Cc4ccc(F)cc4F)s3)cn2[C@H]2CCC(F)(F)C[C@H]21] |
| I-024 | 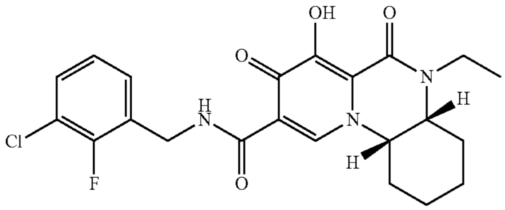 [SMILES: CCN1C(=O)c2c(O)c(=O)c(C(=O)NCc3cccc(Cl)c3F)cn2[C@H]2CCCC[C@H]21] |
TABLE 2-continued
| No. | Structure |
|---|---|
| I-025 | 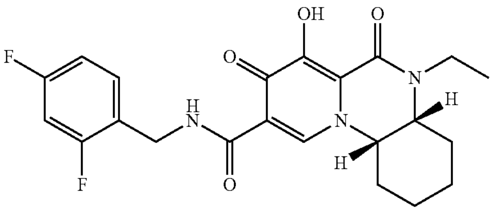 [SMILES: CCN1C(=O)c2c(O)c(=O)c(C(=O)NCc3ccc(F)cc3F)cn2[C@H]2CCCC[C@H]21] |
| I-026 | 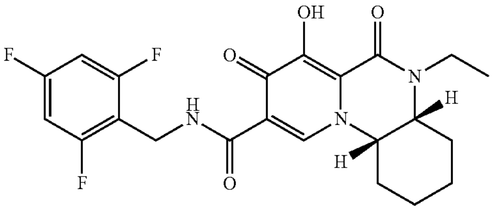 [SMILES: CCN1C(=O)c2c(O)c(=O)c(C(=O)NCc3c(F)cc(F)cc3F)cn2[C@H]2CCCC[C@H]21] |
| I-027 | 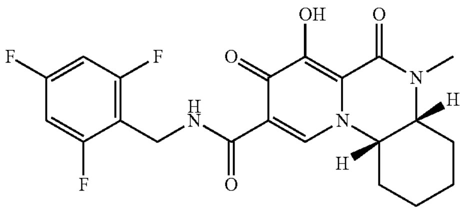 [SMILES: CN1C(=O)c2c(O)c(=O)c(C(=O)NCc3c(F)cc(F)cc3F)cn2[C@H]2CCCC[C@H]21] |
| I-028 | 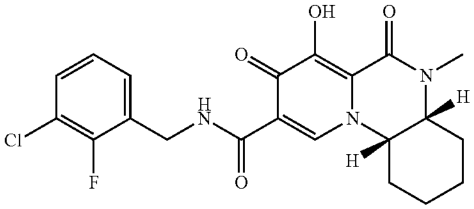 |
| I-029 | 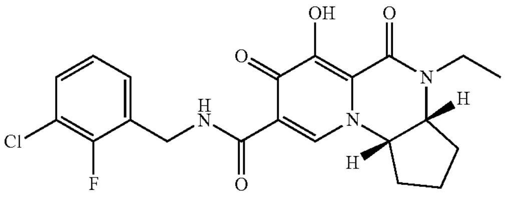 [SMILES: CCN1C(=O)c2c(O)c(=O)c(C(=O)NCc3cccc(Cl)c3F)cn2[C@H]2CCC[C@H]21] |
| I-030 | 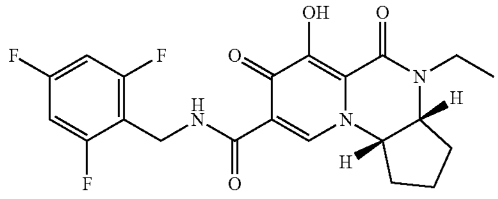 [SMILES: CCN1C(=O)c2c(O)c(=O)c(C(=O)NCc3c(F)cc(F)cc3F)cn2[C@H]2CCC[C@H]21] |
| I-031 | 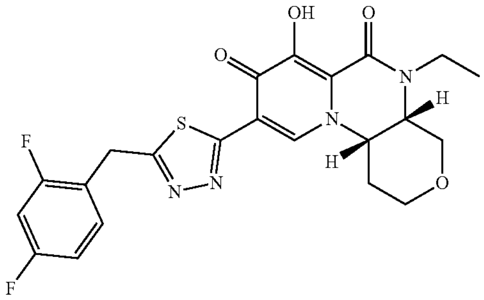 [SMILES: CCN1C(=O)c2c(O)c(=O)c(-c3nnc(Cc4ccc(F)cc4F)s3)cn2[C@H]2CCOC[C@H]21] |

TABLE 2-continued
| No. | Structure |
|---|---|
| I-032 | 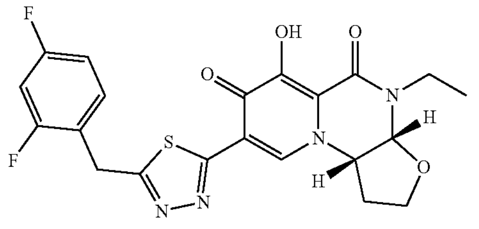 [SMILES: CCN1C(=O)c2c(O)c(=O)c(-c3nnc(Cc4ccc(F)cc4F)s3)cn2[C@H]2CCO[C@H]21] |
TABLE 3
| No. | Structure |
|---|---|
| I-033 | 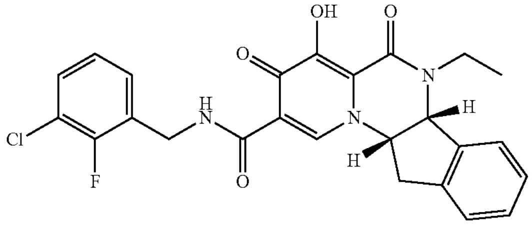 [SMILES: CCN1C(=O)c2c(O)c(=O)c(C(=O)NCc3cccc(Cl)c3F)cn2[C@H]2Cc3ccccc3[C@H]21] |
| I-034 | 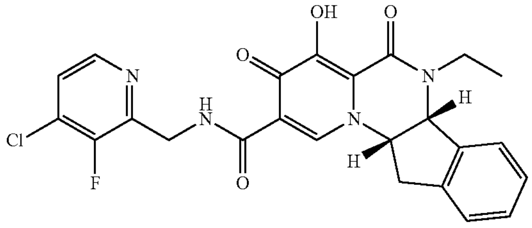 [SMILES: CCN1C(=O)c2c(O)c(=O)c(C(=O)NCc3nccc(Cl)c3F)cn2[C@H]2Cc3ccccc3[C@H]21] |
| I-035 | 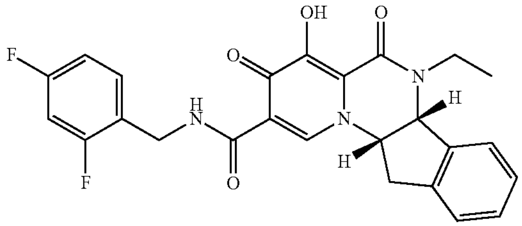 [SMILES: CCN1C(=O)c2c(O)c(=O)c(C(=O)NCc3ccc(F)cc3F)cn2[C@H]2Cc3ccccc3[C@H]21] |
| I-036 | 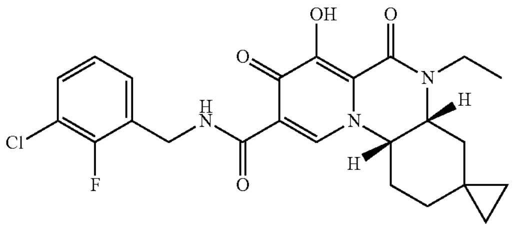 [SMILES: CCN1C(=O)c2c(O)c(=O)c(C(=O)NCc3cccc(Cl)c3F)cn2[C@H]2CCC3(CC3)C[C@H]21] |
| I-037 | 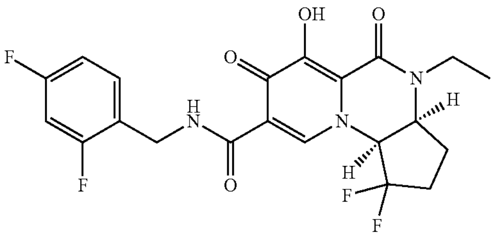 [SMILES: CCN1C(=O)c2c(O)c(=O)c(C(=O)NCc3ccc(F)cc3F)cn2[C@H]2[C@@H]1CCC2(F)F] |
TABLE 3-continued
| No. | Structure |
|---|---|
| I-038 | 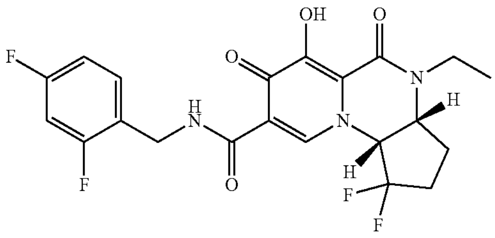 [SMILES: CCN1C(=O)c2c(O)c(=O)c(C(=O)NCc3ccc(F)cc3F)cn2[C@@H]2[C@H]1CCC2(F)F] |
| I-039 | 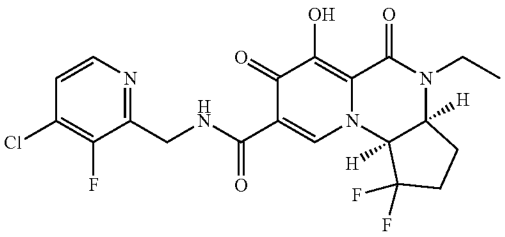 [SMILES: CCN1C(=O)c2c(O)c(=O)c(C(=O)NCc3nccc(Cl)c3F)cn2[C@H]2[C@@H]1CCC2(F)F] |
| I-040 | 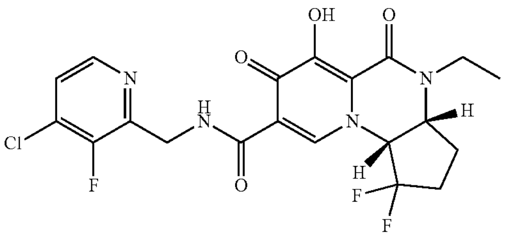 [SMILES: CCN1C(=O)c2c(O)c(=O)c(C(=O)NCc3nccc(Cl)c3F)cn2[C@@H]2[C@H]1CCC2(F)F] |
| I-041 | 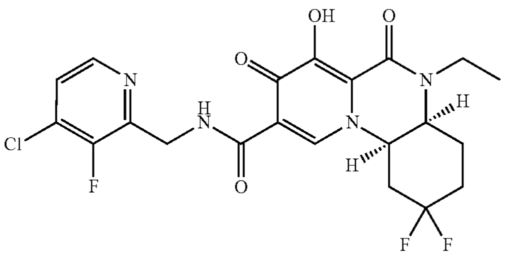 [SMILES: CCN1C(=O)c2c(O)c(=O)c(C(=O)NCc3nccc(Cl)c3F)cn2[C@@H]2CC(F)(F)CC[C@@H]21] |
| I-042 | 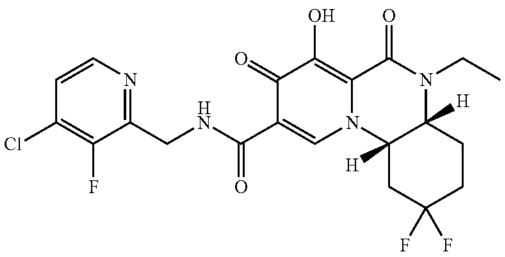 [SMILES: CCN1C(=O)c2c(O)c(=O)c(C(=O)NCc3nccc(Cl)c3F)cn2[C@H]2CC(F)(F)CC[C@H]21] |
| I-043 | 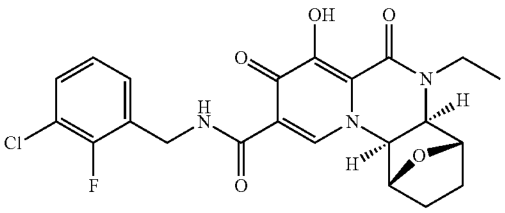 [SMILES: CCN1C(=O)c2c(O)c(=O)c(C(=O)NCc3cccc(Cl)c3F)cn2[C@H]2[C@@H]1[C@@H]1CC[C@H]2O1] |

TABLE 3-continued

| No. | Structure |
|---|---|
| I-044 | 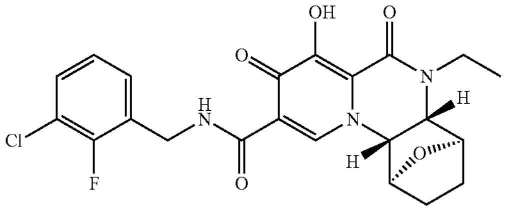 [SMILES: CCN1C(=O)c2c(O)c(=O)c(C(=O)NCc3cccc(Cl)c3F)cn2[C@@H]2[C@H]1[C@H]1CC[C@@H]2O1] |

Physical data on each compound were shown below.

TABLE 4

| No. | NMR |
|---|---|
| I-002 | 1H-NMR (CDCl3) δ: 12.78 (s, 1H), 10.29 (t, J = 5.5 Hz, 1H), 8.35 (s, 1H), 6.70-6.62 (m, 2H), 4.74-4.59 (m, 3H), 4.38-4.29 (m, 1H), 3.91-3.78 (m, 1H), 3.57-3.44 (m, 1H), 2.89-2.56 (m, 4H), 1.29 (t, J = 7.2 Hz, 3H). |
| I-003 | 1H-NMR (CDCl3) δ: 12.73 (s, 1H), 10.87 (t, J = 4.8 Hz, 1H), 8.44 (s, 1H), 8.32 (d, J = 5.1 Hz, 1H), 7.29 (t, J = 5.3 Hz, 1H), 4.93-4.80 (m, 2H), 4.30-4.21 (m, 1H), 4.14 (td, J = 14.1, 7.0 Hz, 1H), 3.84-3.72 (m, 1H), 3.16 (td, J = 14.0, 7.0 Hz, 1H), 2.48-2.34 (m, 1H), 1.99-1.60 (m, 7H), 1.26 (t, J = 7.2 Hz, 3H). |
| I-004 | 1H-NMR (CDCl3) δ: 12.63 (s, 1H), 10.86 (brs, 1H), 8.42 (s, 1H), 8.32 (d, J = 5.1 Hz, 1H), 7.29 (t, J = 5.3 Hz, 1H), 4.96-4.80 (m, 2H), 4.31-4.21 (m, 1H), 3.85-3.70 (m, 1H), 3.17 (s, 3H), 2.38-2.20 (m, 1H), 2.00-1.59 (m, 7H). |
| I-005 | 1H-NMR (CDCl3) δ: 12.65 (s, 1H), 10.46 (brs, 1H), 8.33 (d, J = 1.8 Hz, 1H), 7.32-7.26 (m, 2H), 7.04 (ddd, J = 8.0, 8.0, 1.8 Hz, 1H), 4.71 (d, J = 5.9 Hz, 2H), 4.45-4.29 (m, 3H), 3.09 (td, J = 14.1, 6.9 Hz, 1H), 2.44-2.35 (m, 2H), 2.02-1.70 (m, 4H), 1.21 (t, J = 7.1 Hz, 3H). |
| I-006 | 1H-NMR (CDCl3) δ: 12.58 (s, 1H), 10.34 (brs, 1H), 8.31 (dd, J = 1.8, 0.9 Hz, 1H), 6.66 (t, J = 8.2 Hz, 2H), 4.71-4.61 (m, 2H), 4.38-4.28 (m, 3H), 3.09 (td, J = 14.2, 7.1 Hz, 1H), 2.44-2.35 (m, 2H), 2.03-1.73 (m, 4H), 1.20 (t, J = 7.2 Hz, 3H). |
| I-008 | 1H-NMR (CDCl3) δ: 12.49 (brs, 1H), 10.40 (t, J = 5.3 Hz, 1H), 8.40 (s, 1H), 6.69-6.62 (m, 2H), 4.67 (dd, J = 15.2, 5.8 Hz, 2H), 4.61-4.55 (m, 1H), 4.21 (td, J = 14.2, 7.1 Hz, 1H), 3.86 (dt, J = 21.6, 2.6 Hz, 1H), 3.33 (td, J = 14.1, 7.1 Hz, 1H), 2.86 (d, J = 16.3 Hz, 1H), 2.40-2.28 (m, 1H), 2.05-1.73 (m, 4H), 1.30 (t, J = 7.2 Hz, 3H). |
| I-010 | 1H-NMR (CDCl3) δ: 13.06 (s, 1H), 10.52-10.42 (m, 1H), 8.35 (s, 1H), 6.69-6.61 (m, 2H), 4.75-4.57 (m, 2H), 4.21 (d, J = 8.0 Hz, 1H), 4.02 (td, J = 14.0, 7.0 Hz, 1H), 3.77 (d, J = 7.2 Hz, 1H), 3.24 (td, J = 14.0, 7.0 Hz, 1H), 2.64-2.56 (m, 2H), 1.82-1.69 (m, 2H), 1.55-1.21 (m, 7H). |
| I-011 | 1H-NMR (CDCl3) δ: 12.70 (brs, 1H), 10.44 (brs, 1H), 8.46 (s, 1H), 7.33-7.25 (m, 2H), 7.03 (ddd, J = 8.2, 8.2, 1.5 Hz, 1H), 4.70 (brs, 2H), 4.41 (brs, 1H), 4.02 (dq, J = 14.2, 7.1 Hz, 1H), 3.93-3.79 (m, 1H), 3.26 (dq, J = 14.2, 7.1 Hz, 1H), 2.85-2.81 (m, 1H), 2.50-2.40 (m, 1H), 2.28-2.15 (m, 2H), 2.01-1.86 (m, 2H), 1.32 (t, J = 7.1 Hz, 3H). |
| I-012 | 1H-NMR (CDCl3) δ: 12.65 (brs, 1H), 10.40-10.30 (m, 1H), 8.45 (s, 1H), 6.66 (dd, J = 8.6, 8.6 Hz, 2H), 4.65 (d, J = 5.6 Hz, 2H), 4.40-4.37 (m, 1H), 4.01 (dq, J = 14.4, 7.2 Hz, 1H), 3.88-3.83 (m, 1H), 3.25 (dq, J = 14.4, 7.2 Hz, 1H), 2.86-2.77 (m, 1H), 2.49-2.38 (m, 1H), 2.27-2.13 (m, 2H), 2.00-1.84 (m, 2H), 1.31 (t, J = 7.2 Hz, 3H). |
| I-014 | 1H-NMR(CDCl3) δ: 12.74 (s, 1H), 10.54 (s, 1H), 8.32 (s, 1H), 7.32-7.25 (m, 2H), 7.06-6.98 (m, 1H), 4.83-4.63 (m, 2H), 4.37 (dq, J = 14.1, 7.0 Hz, 1H), 4.20-4.13 (m, 2H), 3.30-3.18 (m, 2H), |

TABLE 4-continued

| No. | NMR |
|---|---|
| | 3.30 (s, 3H), 3.08 (dq J = 14.1, 7.0 Hz, 1H), 2.41 (d, J = 13.1 Hz), 1.97-1.82 (m, 2H), 1.80-1.58 (m, 3H), 1.23 (t, J = 7.2 Hz, 3H) 1.20-1.05 (m, 1H) |
| I-015 | 1H-NMR (CDCl3) δ: 13.04 (s, 1H), 10.56 (t, J = 5.5 Hz, 1H), 8.41 (s, 1H), 7.33-7.23 (m, 2H), 7.06-6.99 (m, 1H), 4.72 (d, J = 6.1 Hz, 2H), 4.49-4.41 (m, 1H), 4.10-4.01 (m, 1H), 3.97-3.84 (m, 1H), 3.50-3.38 (m, 1H), 3.32-3.20 (m, 5H), 2.52-2.25 (m, 3H), 2.19-2.06 (m, 1H), 1.93-1.81 (m, 1H), 1.29 (t, J = 7.2 Hz, 3H). |
| I-017 | 1H-NMR (CDCl3) δ: 12.83 (brs, 1H), 8.69 (s, 1H), 7.34-7.27 (m, 1H), 6.84 (t, J = 8.4 Hz, 2H), 4.45 (s, 2H), 4.37-4.28 (m, 1H), 4.16 (td, J = 14.1, 7.0 Hz, 1H), 3.87-3.76 (m, 1H), 3.17 (td, J = 14.1, 7.1 Hz, 1H), 2.57-2.39 (m, 1H), 2.03-1.64 (m, 7H), 1.28 (t, J = 7.2 Hz, 3H). |
| I-018 | 1H-NMR (CDCl3) δ: 12.74 (brs, 1H), 8.65 (s, 1H), 7.34-7.27 (m, 1H), 6.84 (t, J = 8.5 Hz, 2H), 4.45 (s, 2H), 4.36-4.29 (m, 1H), 3.86 (brs, 1H), 3.18 (s, 3H), 2.43-1.61 (m, 8H). |
| I-019 | 1H-NMR (CDCl3) δ: 13.16 (s, 1H), 8.64 (s, 1H), 7.34-7.27 (m, 1H), 6.88-6.80 (m, 2H), 4.46 (s, 2H), 4.32 (d, J = 8.2 Hz, 1H), 4.05 (td, J = 14.0, 7.0 Hz, 1H), 3.81 (d, J = 7.9 Hz, 1H), 3.26 (td, J = 14.0, 7.0 Hz, 1H), 2.65 (d, J = 11.4 Hz, 2H), 1.86-1.24 (m, 9H). |
| I-020 | 1H-NMR (CDCl3) δ: 13.00 (brs, 1H), 8.63 (s, 1H), 7.30 (dd, J = 15.3, 8.5 Hz, 1H), 6.87-6.81 (m, 2H), 4.52 (dd, J = 12.5, 7.0 Hz, 1H), 4.45 (s, 2H), 4.15 (q, J = 5.2 Hz, 1H), 3.83 (td, J = 14.2, 7.2 Hz, 1H), 3.50 (td, J = 14.1, 7.1 Hz, 1H), 2.36 (dt, J = 23.0, 7.2 Hz, 1H), 2.26-2.04 (m, 3H), 2.00-1.88 (m, 2H), 1.30 (t, J = 7.2 Hz, 3H). |

TABLE 5

| | |
|---|---|
| I-021 | 1H-NMR (CDCl3) δ: 8.60 (brs, 1H), 7.35-7.28 (m, 1H), 6.88-6.80 (m, 2H), 4.73 (brs, 1H), 4.44 (s, 2H), 4.22 (td, J = 14.2, 7.1 Hz, 1H), 3.90 (d, J = 21.7 Hz, 1H), 3.35 (td, J = 14.1, 6.9 Hz, 1H), 2.91 (d, J = 15.8 Hz, 1H), 2.43-2.30 (m, 1H), 2.14-1.79 (m, 4H), 1.33 (t, J = 7.2 Hz, 3H). |
| I-022 | 1H-NMR (DMSO-D6) δ: 12.84 (brs, 1H), 8.71 (brs, 1H), 7.55 (dd, J = 15.4, 8.4 Hz, 1H), 7.29 (ddd, J = 10.2, 10.2, 2.5 Hz, 1H), 7.11 (ddd, J = 8.4, 8.4, 2.5 Hz, 1H), 5.48 (d, J = 23.0 Hz, 1H), 4.61 (brs, 1H), 4.50 (s, 2H), 4.10-4.07 (m, 1H), 3.63-3.14 (m, 1H), 2.42-2.27 (m, 2H), 2.13-1.98 (m, 1H), 1.86-1.75 (m, 2H), 1.59-1.48 (m, 1H), 1.11 (t, J = 7.0 Hz, 3H). |
| I-023 | 1H-NMR (CDCl3) δ: 12.78 (brs, 1H), 8.68 (s, 1H), 7.34-7.30 (m, 1H), 6.87-6.82 (m, 2H), 4.50 (brs, 1H), 4.45 (s, 2H), 4.03 (dq, J = 14.2, 7.1 Hz, 1H), 3.94-3.88 (m, 1H), 3.28 (td, J = 14.2, 7.1 Hz, 1H), 2.93-2.85 (m, 1H), 2.52-2.42 (m, 1H), 2.32-2.20 (m, 2H), 2.15-1.95 (m, 2H), 1.33 (t, J = 7.2 Hz, 3H). |
| I-024 | 1H-NMR (CDCl3) δ: 12.78 (s, 1H), 10.56 (t, J = 5.6 Hz, 1H), 8.43 (s, 1H), 7.33-7.27 (m, 2H), 7.05-7.00 (m, 1H), 4.78-4.63 (m, 2H), 4.30-4.22 (m, 1H), 4.14 (td, J = 14.1, 7.1 Hz, 1H), 3.82-3.73 (m, 1H), 3.16 (td, J = 14.1, 7.0 Hz, 1H), 2.49-2.36 (m, 1H), 1.98-1.60 (m, 7H), 1.27 (t, J = 7.2 Hz, 3H). |
| I-025 | 1H-NMR (CDCl3) δ: 12.77 (s, 1H), 10.56-10.47 (m, 1H), 8.43 (s, 1H), 7.40-7.34 (m, 1H), 6.84-6.77 (m, 2H), 4.72-4.57 (m, 2H), 4.30-4.21 (m, 1H), 4.20-4.07 (m, 1H), 3.84-3.71 (m, 1H), 3.23-3.10 (m, 1H), 2.52-2.32 (m, 1H), 2.00-1.59 (m, 7H), 1.26 (t, J = 7.2 Hz, 3H). |
| I-026 | 1H-NMR (CDCl3) δ: 12.72 (s, 1H), 10.46 (t, J = 5.6 Hz, 1H), 8.42 (s, 1H), 6.69-6.61 (m, 2H), 4.74-4.59 (m, 2H), 4.28-4.19 (m, 1H), 4.12 (td, J = 14.1, 7.1 Hz, 1H), 3.80-3.69 (m, 1H), 3.15 (td, J = 14.1, 7.0 Hz, 1H), 2.52-2.36 (m, 1H), 1.95-1.82 (m, 2H), 1.77-1.60 (m, 5H), 1.26 (t, J = 7.2 Hz, 3H). |

TABLE 5-continued

| | |
|---|---|
| I-027 | 1H-NMR (CDCl3) δ: 12.67 (brs, 1H), 10.50 (brs, 1H), 8.41 (s, 1H), 7.40-7.34 (m, 1H), 6.86-6.75 (m, 2H), 4.71-4.59 (m, 2H), 4.28-4.21 (m, 1H), 3.85-3.75 (m, 1H), 3.17 (s, 3H), 2.38-2.23 (m, 1H), 1.96-1.60 (m, 7H). |
| I-028 | 1H-NMR (CDCl3) δ: 12.69 (s, 1H), 10.54 (t, J = 5.5 Hz, 1H), 8.41 (s, 1H), 7.33-7.27 (m, 2H), 7.05-7.00 (m, 1H), 4.78-4.63 (m, 2H), 4.29-4.21 (m, 1H), 3.85-3.76 (m, 1H), 3.17 (s, 3H), 2.39-2.23 (m, 1H), 1.97-1.61 (m, 7H). |
| I-029 | 1H-NMR (CDCl3) δ: 12.95 (brs, 1H), 10.55 (t, J = 5.4 Hz, 1H), 8.39 (s, 1H), 7.31-7.24 (m, 2H), 7.02 (t, J = 7.8 Hz, 1H), 4.77-4.65 (m, 2H), 4.44 (q, J = 6.5 Hz, 1H), 4.09 (q, J = 5.3 Hz, 1H), 3.82 (td, J = 14.1, 7.0 Hz, 1H), 3.49 (td, J = 14.1, 7.0 Hz, 1H), 2.36-2.25 (m, 1H), 2.22-2.11 (m, 2H), 2.09-1.99 (m, 1H), 1.97-1.85 (m, 2H), 1.29 (t, J = 7.2 Hz, 3H). |
| I-030 | 1H-NMR (CDCl3) δ: 12.90 (brs, 1H), 10.45 (t, J = 5.9 Hz, 1H), 8.38 (s, 1H), 6.69-6.61 (m, 2H), 4.73-4.59 (m, 2H), 4.42 (dd, J = 12.1, 6.1 Hz, 1H), 4.07 (q, J = 5.4 Hz, 1H), 3.81 (td, J = 14.1, 7.0 Hz, 1H), 3.48 (td, J = 14.1, 7.0 Hz, 1H), 2.33-2.24 (m, 1H), 2.21-2.10 (m, 2H), 2.06-1.98 (m, 1H), 1.95-1.86 (m, 2H), 1.28 (t, J = 7.2 Hz, 3H). |
| I-031 | 1H-NMR (CDCl3) δ: 12.77 (brs, 1H), 8.59 (s, 1H), 7.37-7.28 (m, 1H), 6.89-6.80 (m, 2H), 4.48-4.40 (m, 3H), 4.32-4.24 (m, 1H), 4.23-3.97 (m, 3H), 3.78-3.64 (m, 2H), 3.49-3.37 (m, 1H), 2.40-2.26 (m, 1H), 2.03-1.93 (m, 1H), 1.29 (t, J = 7.2 Hz, 3H). |
| I-032 | 1H-NMR (CDCl3) δ: 12.78 (s, 1H), 8.61 (s, 1H), 7.37-7.21 (m, 1H), 6.90-6.79 (m, 2H), 5.54 (d, J = 5.3 Hz, 1H), 4.88-4.75 (m, 1H), 4.45 (s, 2H), 4.22-4.05 (m, 2H), 3.85-3.72 (m, 1H), 3.71-3.57 (m, 1H), 2.80-2.64 (m, 1H), 2.33-2.17 (m, 1H), 1.30 (t, J = 7.2 Hz, 3H). |

TABLE 6

| No. | MS | Charge |
|---|---|---|
| I-033 | 482 | M + H |
| I-034 | 483 | M + H |
| I-035 | 466 | M + H |
| I-036 | 474 | M + H |
| I-037 | 454 | M + H |
| I-038 | 454 | M + H |
| I-039 | 471 | M + H |
| I-040 | 471 | M + H |
| I-041 | 485 | M + H |
| I-042 | 485 | M + H |
| I-043 | 462 | M + H |
| I-044 | 462 | M + H |

Biological test examples of the compound of the present invention were described below.

Test Example 1: Anti-HIV Activity

Serial dilutions of a test sample were prepared in a 384-well microplate by a dispensing machine. $6.25\times10^4$ cells/mL of a MT-4 cell suspension was dispensed at 20 μL/well to the plate containing the test sample. Then, an HIV virus solution was dispensed at 20 μL/well. The plate was mixed with a plate mixer and cultured for 4 days in a $CO_2$ incubator. On day 4 of culture, CellTiter-Glo or CellTiter-Glo 2.0 was dispensed at 20 μL/well. The plate was reacted while being stirred with the plate mixer at room temperature for about 15 minutes. The amount of luminescence of the plate after the reaction was measured with a microplate reader. A 50% HIV inhibitory concentration (EC50) was determined from a concentration-dependent curve using the following 4 parameter logistic curve fitting model.

$$y=A+((B-A)/(1+((C/x)^D)))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

(Results)

TABLE 7

| NO. | EC50_nM |
|---|---|
| I-001 | 1.40 |
| I-002 | 1.50 |
| I-003 | 3.90 |
| I-004 | 3.30 |
| I-005 | 1.00 |
| I-006 | 0.63 |
| I-007 | 0.70 |
| I-008 | 0.52 |
| I-009 | 6.50 |
| I-010 | 5.20 |
| I-011 | 9.00 |
| I-012 | 0.93 |
| I-013 | 2.50 |
| I-014 | 3.80 |
| I-015 | 2.50 |
| I-016 | 2.50 |
| I-017 | 4.20 |
| I-018 | 2.30 |
| I-019 | 8.20 |
| I-020 | 5.00 |
| I-021 | 3.60 |
| I-022 | 5.30 |
| I-023 | 4.60 |
| I-024 | 1.90 |
| I-025 | 2.10 |
| I-026 | 1.30 |
| I-027 | 0.70 |
| I-028 | 1.20 |
| I-029 | 2.20 |
| I-030 | 2.60 |

Test Example 1B: Anti-HIV Activity

Serial dilutions of a test sample were prepared in a 96-well microplate (50 μL/well). $2.5\times10^5$ cells/mL of a MT-4 cell suspension was dispensed at 100 μL/well to the plate containing the test sample. Then, an HIV virus solution was dispensed at 50 μL/well. The plate was mixed with a plate mixer and cultured for 4 days in a $CO_2$ incubator. An MTT (3-(4,5-dimethylthiazol-2-yl)-2,5-diphenyltetrazolium bromide) solution was dispensed at 30 μL/well. The plate was reacted for 1 hour in a $CO_2$ incubator. 150 μL of the supernatant was removed from each well so as not to take up the cells. 150 μL of a cell lysis solution was added to each well and well mixed with a plate mixer until the cells were completely lysed. The absorbance of the mixed plate was measured at two wavelengths of 560 nm and 690 nm using a microplate reader. A 50% HIV inhibitory concentration (EC50) was determined from a concentration-dependent curve using the following 4 parameter logistic curve fitting model.

$$y=A+((B-A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

(Results)

TABLE 8

| NO. | EC50_nM |
|---|---|
| I-033 | 9.70 |
| I-034 | 12.00 |
| I-035 | 5.40 |
| I-036 | 7.10 |
| I-037 | 3.60 |
| I-038 | 4.30 |
| I-039 | 9.80 |
| I-040 | 13.00 |
| I-041 | 12.00 |
| I-042 | 7.90 |
| I-043 | 6.20 |
| I-044 | 7.00 |

From the above test results, it became clear that the compound of the present invention has usefulness as an HIV drug since it shows high anti-HIV activity.

Test Example 2: Resistance Evaluation Test

Serial dilutions of a test sample were prepared in a 96-well microplate (50 μL/well). $2.5\times10^5$ cells/mL of a HeLa-CD4 cell suspension was dispensed at 100 μL/well to the plate containing the test sample. Then, an HIV virus solution (wild strain and mutant strain) was dispensed at 50 μL/well. The plate was mixed with a plate mixer and cultured for 3 days in a $CO_2$ incubator. The culture supernatant in each well was removed by suction. A cell lysis buffer was dispensed at 100 μL/well, and the plate was frozen in a freezer (−80° C.). The plate frozen in a freezer was thawed at room temperature, then mixed with a plate mixer, and centrifuged at 1,200 rpm for 5 minutes. Beta-Glo Reagent was dispensed at 20 μL/well to a 384-well microplate, 2 μL of the supernatant of each well (diluted as necessary) of the plate after centrifugation was added, and then the mixture was reacted at room temperature for about 30 minutes. The amount of luminescence of the plate after the reaction was measured with a microplate reader. A 50% HIV inhibitory concentration (EC50) was determined from a concentration-dependent curve using the following 4 parameter logistic curve fitting model.

$$y=A+((B-A)/(1+((C/x)^D)))$$

A=minimum rate of inhibition (negative control, 0%)

B=maximum rate of inhibition (positive control, 100%)

C=compound concentration at an inflection point

D=slope coefficient x=compound concentration y=rate of inhibition (%)

The degree of resistance (fold change (FC)) of each mutant strain was calculated according to the following expression.

FC=EC50 of the mutant strain/EC50 of the wild strain (Results)

FC for the mutant strains (E92Q/E138T/G140S/Q148H)

Compound I-005: 6.7

Compound I-014: 4.1

Compound I-017: 6.0

Compound I-020: 7.7

From the above test results, the compound of the present invention has high resistance barrier and cannot easily cause an HIV-resistant virus.

Test Example 3: CYP Inhibition Test

The degrees at which the amounts of respective metabolites produced were inhibited by the compound of the present invention were evaluated in commercially available pooled human liver microsomes by using the O-deethylation of 7-ethoxyresorufin (CYP1A2), the methyl-hydroxylation of tolbutamide (CYP2C9), 4'-hydroxylation of mephenytoin (CYP2C19), the O-demethylation of dextromethorphan (CYP2D6), and the hydroxylation of terfenadine (CYP3A4), which are the typical substrate metabolism reactions of five human major CYP molecular species (CYP1A2, CYP2C9, CYP2C19, CYP2D6, and CYP3A4), as indexes.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), and 1 μmol/L terfenadine (CYP3A4); reaction time, 15 minutes; reaction temperature, 37° C.; enzyme, pooled human liver microsomes, 0.2 mg protein/mL; concentrations of the compound of the present invention, 1, 5, 10, and 20 μmol/L (4 points).

Each of the five substrates, the human liver microsomes, and the compound of the present invention were added according to the recipe described above into a 50 mmol/L Hepes buffer solution in a 96-well plate, and a coenzyme NADPH was added thereto to start the metabolism reactions serving as indexes. After the incubation at 37° C. for 15 minutes, a methanol/acetonitrile=1/1 (V/V) solution was added to stop the reaction. After centrifugation at 3000 rpm for 15 minutes, resorufin (CYP1A2 metabolite) in the centrifugation supernatant was quantified using a fluorescence multilabel counter or LC/MS/MS, and tolbutamide hydroxide (CYP2C9 metabolite), mephenytoin 4'-hydroxide (CYP2C19 metabolite), dextrorphan (CYP2D6 metabolite), and terfenadine alcohol (CYP3A4 metabolite) in the centrifugation supernatants were quantified by LC/MS/MS.

Only a solvent DMSO used for dissolving the compound was added to the reaction solution instead of the compound of the present invention, and the mixture was used as a control (100%). Remaining activity (%) was calculated, and $IC_{50}$ was calculated by inverse estimation based on a logistic model using the concentrations and the rates of suppression.

Test Example 4: CYP3A4 (MDZ) MBI Test

This test as to the inhibition of CYP3A4 by the compound of the present invention is to evaluate mechanism based inhibition (MBI) ability from enhancement in inhibitory effect, caused by a metabolism reaction, of the compound of the present invention. CYP3A4 inhibition was evaluated using pooled human liver microsomes by 1-hydroxylation reaction of midazolam (MDZ) as a marker reaction.

Reaction conditions are as follows: substrate, 10 μmol/L MDZ; prereaction time, 0 or 30 minutes; substrate metabolism reaction time, 2 minutes; reaction temperature, 37° C.; pooled human liver microsomes, 0.5 mg/mL for the prereaction, and 0.05 mg/mL (10-fold dilution) for the reaction; concentrations of the compound of the present invention for the prereaction, 1, 5, 10, and 20 μmol/L (4 points) or 0.83, 5, 10, and 20 μmol/L (4 points).

The pooled human liver microsomes and a solution of the compound of the present invention were added according to the recipe of the prereaction described above into a K-Pi buffer solution (pH 7.4) as a prereaction solution in a 96-well plate. A portion thereof was transferred to another 96-well plate so as to be diluted by 1/10 with a K-Pi buffer solution containing the substrate. A coenzyme NADPH was added thereto to start the reaction serving as an index (there was no pre-reaction: 0-min preincubation). After reaction for a given time, the reaction was terminated by the addition of a solution of methanol/acetonitrile=1/1 (V/V). NADPH was also added to the remaining prereaction solution to start prereaction (there was pre-reaction: 30-min preincubation). After prereaction for a given time, a portion thereof was transferred to another plate so as to be diluted by 1/10 with a K-Pi buffer solution containing the substrate, to start the reaction serving as an index. After a predetermined time of a reaction, methanol/acetonitrile=1/1 (v/v) solution was added to stop the reaction. After centrifuged at 3000 rpm for 15 minutes, 1-hydroxymidazolam in the supernatant was quantified by LC/MS/MS.

Only a solvent DMSO used for dissolving the compound was added to the reaction solution instead of the compound of the present invention, and the mixture was used as a control (100%). Remaining activity (%) at the time of the addition of the compound of the present invention at each concentration was calculated, and IC was calculated by inverse estimation based on a logistic model using the concentrations and the rates of suppression. A shifted IC value is calculated from IC from the 0 min preincubation/IC from the 30-min preincubation. Shifted IC of 1.5 or more is graded as positive (+), and shifted IC of 1.0 or less is graded as negative (−).

(Results)

Compound I-022: (−)

Test Example 5: BA Test

Experimental Material and Method to Study Oral Absorbability (1) Animals used: Rats were used.

(2) Breeding conditions: The rats were allowed to freely take solid food and sterilized tap water.

(3) Dose and grouping setting: A predetermined dose was orally administered and intravenously administered. Groups were set as follows: (dose was changed on a compound basis)

Oral administration: 2 to 60 μmol/kg or 1 to 30 mg/kg (n=2 or 3)

Intravenous administration: 1 to 30 μmol/kg or 0.5 to 10 mg/kg (n=2 or 3)

(4) Preparation of dosing solution: The test sample was administered as a solution or a suspension for the oral administration. The test sample was solubilized and administered for the intravenous administration.

(5) Administration method: The test sample was forcedly administered into the stomach through an oral probe for the oral administration. The test sample was administered to the tail vein through a syringe with an injection needle for the intravenous administration.

(6) Evaluation item: Blood was collected over time, and the concentration of the compound of the present invention in plasma was measured using LC/MS/MS.

(7) Statistical analysis: An area under concentration in plasma-time curve (AUC) was calculated as to change in the concentration of the compound of the present invention in plasma by the moment analysis method, and the bioavailability (BA) of the compound of the present invention was calculated from the dose ratio and AUC ratio between the oral administration group and the intravenous administration group.

Test Example 6: Clearance Evaluation Test

Experimental Material and Method (1) Animals used: Rats were used.

(2) Breeding conditions: The rats were allowed to freely take solid food and sterilized tap water.

(3) Dose and grouping setting: A predetermined dose was intravenously administered. Groups were set as follows:

Intravenous administration: 1 μmol/kg (n=2)

(4) Preparation of dosing solution: The test sample was solubilized using a solvent of dimethyl sulfoxide/propylene glycol=1/1 and administered.

(5) Administration method: The test sample was administered to the tail vein through a syringe with an injection needle.

(6) Evaluation item: Blood was collected over time, and the concentration of the compound of the present invention in plasma was measured using LC/MS/MS.

(7) Statistical analysis: Total body clearance (CLtot) and elimination half-life (t½) were calculated as to change in the concentration of the compound of the present invention in plasma by the moment analysis method.

(Results)

Compound I-005: 0.117 mL/min/kg, 10.9 hr

Compound I-017: 0.0712 mL/min/kg, 15.3 hr

From the above results, the compound of the present invention is useful as a long-acting integrase inhibitor since it has small clearance and a long elimination half-life.

Test Example 7: Metabolism Stability Test

Commercially available pooled human liver microsomes were reacted with the compound of the present invention for a given time. A residual rate was calculated by the comparison between the reacted sample and an unreacted sample to evaluate the degree at which the compound of the present invention was metabolized in the liver.

The compound was reacted at 37° C. for 0 minutes or 30 minutes in the presence of 1 mmol/L NADPH in 0.2 mL of a buffer solution (50 mmol/L Tris-HCl pH 7.4, 150 mmol/L potassium chloride, and 10 mmol/L magnesium chloride) containing 0.5 mg protein/mL of the human liver microsomes (oxidative reaction). After the reaction, 50 μL of the reaction solution was added to 100 μL of a solution of methanol/acetonitrile=1/1 (v/v), and the mixture was mixed and centrifuged at 3000 rpm for 15 minutes. The compound of the present invention in the centrifugation supernatant was quantified by LC/MS/MS or solid-phase extraction (SPE)/MS. The amount of the compound of the present invention remaining after the reaction was calculated with the amount of the compound at 0 minutes of the reaction defined as 100%.

(Results)

Remaining rates at a compound concentration of 0.5 μmol/L are shown below.

Compound I-003: 91.7%

Compound I-020: 74.6%

Test Example 8: Fluctuation Ames Test

Mutagenicity of the compound of the present invention was evaluated.

20 μL of cryopreserved *Salmonella typhimurium* (TA98 strain and TA100 strain) was inoculated to 10 mL of a liquid nutrient medium (2.5% Oxoid nutrient broth No. 2) and shake-precultured at 37° C. for 10 hours. 7.70 to 8.00 mL of a bacterial solution of the TA98 strain was centrifuged (2000×g, 10 minutes) to remove a culturing solution. The bacterium was suspended in Micro F buffer solution ($K_2HPO_4$: 3.5 g/L, $KH_2PO_4$: 1 g/L, $(NH_4)_2SO_4$: 1 g/L, trisodium citrate dihydrate: 0.25 g/L, and $MgSO_4.7H_2O$: 0.1 g/L) in the same volume as that of the bacterial solution used in the centrifugation and added to 120 mL of an exposure medium (Micro F buffer solution containing biotin: 8 μg/mL, histidine: 0.2 μg/mL, and glucose: 8 mg/mL). 3.10 to 3.42 mL of the bacterial solution of the TA100 strain was added to 120 to 130 mL of an exposure medium to prepare a test bacterial solution. Each 12 μL of DMSO solution of the compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL, of the test bacterial solution (a mixed solution of 498 μL, of the test bacterial solution and 90 μL of S9 mix under the metabolism activating condition) were mixed, and this was shaking-cultured at 37° C. for 90 minutes. 460 μL of the bacterial solution exposed to the compound of the present invention was mixed with 2300 μL of an indicator medium (Micro F buffer solution containing biotin: 8 μg/mL, histidine: 0.2 μg/mL, glucose: 8 mg/mL, and bromocresol purple: 37.5 μg/mL), and the mixture is dispensed at 50 μL/well and 48 wells/dose to a microplate and static cultured at 37° C. for 3 days. Since a well containing a bacterium which had obtained the proliferation ability by mutation of an amino acid (histidine) synthesizing enzyme gene turns from purple to yellow due to a pH change, the bacterium proliferation well which had turned to yellow in 48 wells per dose was counted, and was assessed by comparing with a negative control group. Negativity to mutagenicity is indicated by (−), and positivity thereto is indicated by (+).

Test Example 9: hERG Test

For the purpose of assessing risk of an electrocardiogram QT interval prolongation of the compound of the present invention, effects of the compound of the present invention on delayed rectifier $K^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S), $I_{Kr}$ induced by application of a leak potential of −50 mV followed by depolarization pulse stimulation at +20 mV for 2 seconds and, further, repolarization pulse stimulation at −50 mV for 2 seconds, was recorded. An extracellular fluid (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4) adjusted to 0.1% with dimethyl sulfoxide was used as a vehicle to apply the vehicle and the extracellular fluid containing the compound of the present invention dissolved at a concentration of interest to the cells under conditions of room temperature for 7 minutes or longer. From the obtained $I_{Kr}$, the absolute value of the maximum tail current based on the current value at the membrane potential where the cells have been kept was measured using analytical software (QPatch Assay software; Sophion Bioscience A/S). The maximum tail current after the application of the compound of the present invention with respect to the maximum tail current after the application of the vehicle was further calculated as the rate of inhibition to evaluate the influence of the compound of the present invention on $I_{Kr}$.

Test Example 10: Solubility Test

The solubility of the compound of the present invention was determined under conditions of 1% DMSO addition. A 10 mmol/L solution of the compound was prepared with DMSO. 2 μL of the solution of the compound of the present invention was added to 198 μL each of a JP-1 fluid and a JP-2 fluid. After shaking at room temperature for 1 hour, the mixed solutions were filtered by suction. The filtrates were diluted 10- or 100-fold with methanol/water=1/1 (V/V) or acetonitrile/methanol/water=1/1/2 (V/V/V), and concentrations in the filtrates were measured by the absolute calibration curve method using LC/MS or solid-phase extraction (SPE)/MS.

The composition of the JP-1 fluid is as below.

Water is added to 2.0 g of sodium chloride and 7.0 mL of hydrochloric acid to bring the amount to 1000 mL.

The composition of the JP-2 fluid is as below.

3.40 g of potassium dihydrogen phosphate and 3.55 g of dibasic sodium phosphate anhydrous are dissolved in water to bring the amount to 1000 mL, and to 1 volume of the resultant, 1 volume of water is added.

Test Example 11: Powder Solubility Test

An appropriate amount of the compound of the present invention is placed in appropriate containers, and 200 μL of a JP-1 fluid (water is added to 2.0 g of sodium chloride and 7.0 mL of hydrochloric acid to bring the amount to 1000 mL), a JP-2 fluid (3.40 g of potassium dihydrogen phosphate and 3.55 g of dibasic sodium phosphate anhydrous are dissolved in water to bring the amount to 1000 mL, and to 1 volume of the resultant, 1 volume of water is added), or 20 mmol/L sodium taurocholate (TCA) in a JP-2 fluid (a JP-2 fluid is added to 1.08 g of TCA to bring the amount to 100 mL) was added to each container. When the whole amount was dissolved after the test solution addition, the compound of the present invention was appropriately further added. The containers were hermetically sealed, shaken at 37° C. for 1 hour, and then filtered. Each filtrate was diluted 2-fold by the addition of 100 μL of methanol to 100 μL of the filtrate. The dilution rate was changed as necessary. The absence of air bubbles and deposits was confirmed, and the containers were hermetically sealed and shaken. The compound of the present invention was quantified by the absolute calibration curve method using HPLC.

Test Example 12: Ames Test

The compound of the present invention is evaluated for its mutagenicity by the Ames test with *Salmonella typhimurium* TA98, TA100, TA1535 and TA1537 strains and an *Escherichia coli* WP2uvrA strain as test bacterial strains. 0.1 mL of a DMSO solution of the compound of the present invention is mixed with 0.5 mL of S9 mix under metabolic activation conditions or 0.5 mL of a phosphate buffer solution and 0.1 mL of each test bacterial solution under non-metabolic activation conditions, and the mixture is overlaid on a minimum glucose agar plate together with 2 mL of soft agar for overlay containing histidine and biotin, or tryptophan. At the same time therewith, a similar test is also conducted as to a negative control substance (DMSO) and a positive control substance (2-(2-furyl-3-(5-nitro-2-furyDacrylamide, sodium azide, 9-aminoacridine, or 2-aminoanthracene).

After culture at 37° C. for 48 hours, revertant colonies that have appeared are counted and evaluated by comparison with the negative control group. When the number of revertant colonies increases in a concentration-dependent manner and becomes twice or more the number of colonies of the negative control group, positivity (+) is determined.

Test Example 13: Nav Test

For the purpose of assessing proarrhythmic risk of the compound of the present invention, effects of the compound of the present invention on $Na^+$ current ($I_{Na}$), which plays an important role in the myocardial depolarization process, was studied using HEK cells expressing Voltage gated sodium channel (Nav 1.5 channel) encoded by SCNSA gene.

After a cell was retained at a membrane potential of −100 mV by the whole cell patch clamp method using an automated patch clamp system (QPatch; Sophion Bioscience A/S), $I_{Na}$ induced by depolarization pulse stimulation at −10 mV for 20 milliseconds was recorded. An extracellular fluid (NaCl: 145 mmol/L, KCl 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, tetraethylammonium hydroxide (TEA): 10 mmol/L, pH=7.4) adjusted to 0.3% with dimethyl sulfoxide was used as a vehicle to apply the vehicle and the extracellular fluid containing the compound of the present invention dissolved at a concentration of interest to the cells under conditions of room temperature for 5 minutes or longer. From the obtained $I_{Na}$, the absolute value of the maximum peak current based on the current value at the membrane potential where the cells have been kept was measured using analytical software (QPatch Assay software; Sophion Bioscience A/S). The ratio of the maximum peak current at the time of applying the compound of the present invention to the maximum peak current at the time of applying the vehicle and the electric charge amount at the time of applying the compound of the present invention with respect to the electric charge amount at the time of applying vehicle were calculated, and the influence of the compound of the present invention on $I_{Na}$ was evaluated.

(Results)

Compound I-017: maximum current amount increase rate 95.6%, electric charge amount increase rate 133%

Compound I-022: maximum current amount increase rate 93.1%, electric charge amount increase rate 137%

From the above results, a clear increase in current and electric charge is not recognized, and the compound of the present invention has a low concern of arrhythmia attributable to an increase in Na current.

Test Example 14: Anti-HIV Activity Evaluation Test Using Peripheral Blood Mononuclear Cell (PBMC) of Healthy People Serial dilutions of a test sample were prepared in a 96-well microplate (50 μL/well). PBMC stimulated with $1.0\times10^5$ cells/well of Phytohemagglutinin (PHA) and an HIV virus solution were mixed for the necessary number of wells and reacted at 37° C. for 1 hour. After the reaction, the cell suspension was centrifuged to discard the supernatant, the infected cells were dispersed in a culturing solution for the necessary number of wells at 150 μL/well, and the resultant solution was dispensed at 150 μL/well to a 96-well microplate containing the test sample. The plate was mixed with a plate mixer and cultured for 4 days in a $CO_2$ incubator. The reverse transcriptase activity in the culturing solution. A 90% HIV inhibitory concentration (EC90) was determined from a concentration-dependent curve using the following 4 parameter logistic curve fitting model.

$$y=A+((B-A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

Test Example 14: Anti-HIV Activity Evaluation Test in Presence of Human Serum Protein Serial dilutions of a test sample were prepared in a 384-well microplate by a dispensing machine. A human serum protein solution (human serum protein concentration 50%) was dispensed at 20 μL/well to a 384-well microplate containing the test sample and left to stand still at room temperature for 1 hour. A culturing solution was dispensed at 20 μL/well to a plate for the absence of serum. 1 mL of $3.0\times10^6$ cells/mL of MT-4 cells and a 300 μL HIV virus solution were mixed and reacted at 37° C. for 1 hour. After the reaction, the cell suspension was centrifuged to discard the supernatant, the infected cells were dispersed in 40 mL of a culturing solution and the resultant solution was dispensed at 20 μL/well to a 384-well microplate containing the test sample and the human serum protein (human serum protein final concentration: 25%). The plate was mixed with a plate mixer and cultured for 4 days in a $CO_2$ incubator. On day 4 of culture, CellTiter-Glo or CellTiter-Glo 2.0 was dispensed at 20 μL/well. The plate was reacted while being stirred with the plate mixer at room temperature for about 15 minutes. The amount of luminescence of the plate after the reaction was measured with a microplate reader. A 50% HIV inhibitory concentration (EC50) was determined from a concentration-dependent curve using the following 4 parameter logistic curve fitting model.

$$y=A+((B-A)/(1+((C/x)^D)))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

The potency shift (PS) was calculated on the basis of the following calculation formula. The PS is an extrapolated value of the human serum protein concentration of 100%.

PS=4×(EC50 in the presence of 25% human serum protein/EC50 in the absence of human serum protein)

(Results)

The PS in the presence of human serum protein is shown in the table (100% extrapolated value).

Compound I-005: 104

Compound I-020: 29

Preparation Example

The compound of the present invention can be administered as a pharmaceutical composition through an arbitrary route, particularly, enterally, for example, orally, in the form of, for example, a tablet or a capsule, parenterally in the form of, for example, an injection or a suspension, locally in the form of, for example, a lotion, a gel, an ointment or a cream, or in a transnasal form or a suppository form. The pharmaceutical composition comprising the compound of the present invention in the free form or in the form of a pharmaceutically acceptable salt can be produced together with at least one kind of pharmaceutically acceptable carrier or diluent by a conventional method such as a mixing, granulating, or coating method. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

INDUSTRIAL APPLICABILITY

The compound of the present invention has integrase inhibitory activity and/or cell proliferation inhibitory activity against viruses, particularly, HIV. Accordingly, the compound of the present invention is useful in preventing or treating various diseases, viral infections (e.g., AIDS), and the like with which integrase is associated.

The invention claimed is:

1. A compound represented by the following Formula:

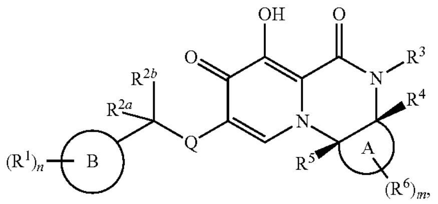

wherein ring A is a C5-C7 non-aromatic carbocycle, which may be further fused with a phenyl ring, a 3- to 7-membered non-aromatic carbocycle, or a 3- to 7-membered non-aromatic heterocycle, and which may form a spiro ring of a 3- to 7-membered non-aromatic carbocycle and a 3- to 7-membered non-aromatic heterocycle;

ring B is a phenyl ring or a pyridinyl ring;

Q is of the following rings, wherein the left bond binds to $CR^{2a}R^{2b}$, (1)

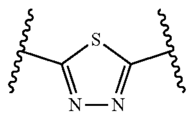

(2)

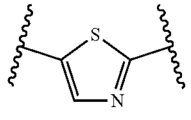

(20)

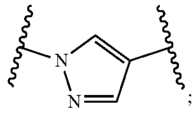

;

$R^1$ is each independently halogen, C1-4alkyl, haloC1-4alkyl, C1-4alkyloxy, cyano, or haloC1-4alkyloxy;

$R^{2a}$ and $R^{2b}$ are each independently hydrogen, C1-4alkyl, or haloC1-4alkyl;

$R^3$ is C1-4alkyl or haloC1-4alkyl;

$R^4$ and $R^5$ are each independently hydrogen or C1-4alkyl;

$R^6$ is each independently halogen, C1-4alkyl, haloC1-4alkyl, C1-4alkyloxy, haloC1-4alkyloxy, or C1-4alkyloxyC1-4alkyl; or two $R^6$s bonded to a non-adjacent atom may be taken together with each other to form a $C_1$-$C_3$ bridge which may have an intervening heteroatom;

n is an integer of 1 to 3; and m is an integer of 0 to 3;

wherein non-aromatic heterocycle means non-aromatic heterocycle containing 1 or 2 heteroatoms selected from the group consisting of O, S and N, or a pharmaceutically acceptable salt thereof.

2. The compound according to claim 1, or a pharmaceutically acceptable salt thereof, wherein the ring A is a C5-C7 non-aromatic carbocycle, and $R^6$ is each independently halogen, C1-4alkyl, haloC1-4alkyl, C1-4alkyloxy, haloC1-4alkyloxy, or C1-4alkyloxyC1-4alkyl, or two $R^6$s bonded to a non-adjacent atom are taken together with each other to form a C1-C3 bridge.

3. The compound according to claim 1, or a pharmaceutically acceptable salt thereof, wherein $R^4$ and $R^5$ are each hydrogen.

4. The compound according to claim 1, or a pharmaceutically acceptable salt thereof, wherein $R^3$ is C1-4alkyl.

5. The compound according to claim 1, or a pharmaceutically acceptable salt thereof, wherein $R^1$ is each independently halogen.

6. The compound according to claim 1, or a pharmaceutically acceptable salt thereof, wherein $R^{2a}$ is hydrogen and $R^{2b}$ is hydrogen or C1-4alkyl.

7. The compound according to claim 1, or a pharmaceutically acceptable salt thereof, wherein the ring B is a phenyl ring.

8. A pharmaceutical composition comprising an effective amount of the compound according to claim 1 or a pharmaceutically acceptable salt thereof, and a pharmaceutically acceptable additive, carrier or diluent.

9. A compound represented by Formula (IA):

(IA)

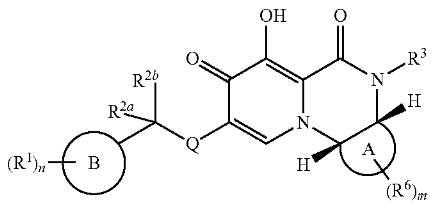

wherein ring A is a C5-C6 non-aromatic carbocycle;

ring B is a phenyl ring or a pyridinyl ring;

Q is one of the following rings, wherein the left bond binds to $CR^{2a}R^{2b}$, (1)

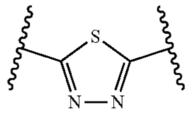

-continued

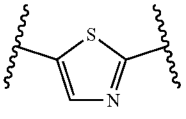

(2)

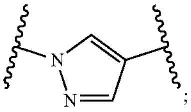

(20)

;

$R^1$ is each independently halogen, C1-4alkyl, haloC1-4alkyl, C1-4alkyloxy, cyano, or haloC1-4alkyloxy;

$R^{2a}$ and $R^{2b}$ are each independently hydrogen, C1-4alkyl, or haloC1-4alkyl;

$R^3$ is C1-4alkyl or haloC1-4alkyl;

$R^6$ is each independently halogen C1-4alkyl, haloC1-4alkyl, C1-4alkyloxy, or haloC1-4alkyloxy; or two $R^6$s bonded to a non-adjacent atom may be taken together with each other to form a $C_1$-$C_3$ bridge;

n is an integer of 1 to 3; and m is an integer of 0 to 2;

or a pharmaceutically acceptable salt thereof.

10. The compound according to claim 9, or a pharmaceutically acceptable salt thereof, wherein $R^3$ is C1-4alkl.

11. The compound according to claim 10, or a pharmaceutically acceptable salt thereof, wherein $R^1$ is each independently halogen.

12. The compound according to claim 9, or a pharmaceutically acceptable salt thereof, wherein $R^{2a}$ is hydrogen and $R^{2b}$ is hydrogen or C1-4alkyl.

13. The compound according to claim 9, or a pharmaceutically acceptable salt thereof, wherein the ring B is a phenyl ring;

$R^1$ is each independently halogen;

$R^{2a}$ is hydrogen and $R^{2b}$ is hydrogen or C1-4alkyl; and $R^3$ is C1-4alkyl.

14. A pharmaceutical composition comprising an effective amount of the compound according to claim 9 or a pharmaceutically acceptable salt thereof, and a pharmaceutically acceptable additive, carrier or diluent.

* * * * *